United States Patent
Williams

(10) Patent No.: US 10,973,557 B2
(45) Date of Patent: Apr. 13, 2021

(54) SPINAL ROD IMPLANT EXTENSION

(71) Applicant: Seth K. Williams, Madison, WI (US)

(72) Inventor: Seth K. Williams, Madison, WI (US)

(73) Assignee: Seth K. Williams, Madison, WI (US)

( * ) Notice: Subject to any disclaimer, the term of this patent is extended or adjusted under 35 U.S.C. 154(b) by 45 days.

(21) Appl. No.: 16/247,872

(22) Filed: Jan. 15, 2019

(65) Prior Publication Data

US 2019/0142469 A1    May 16, 2019

Related U.S. Application Data

(63) Continuation-in-part of application No. 15/250,394, filed on Aug. 29, 2016, now Pat. No. 10,194,953.

(60) Provisional application No. 62/241,987, filed on Oct. 15, 2015.

(51) Int. Cl.
*A61B 17/70* (2006.01)

(52) U.S. Cl.
CPC ........ *A61B 17/705* (2013.01); *A61B 17/7005* (2013.01); *A61B 17/7032* (2013.01); *A61B 17/7034* (2013.01); *A61B 17/7047* (2013.01)

(58) Field of Classification Search
CPC .............. A61B 17/705; A61B 17/7005; A61B 17/7032; A61B 17/7034
See application file for complete search history.

(56) References Cited

U.S. PATENT DOCUMENTS

| | | | | |
|---|---|---|---|---|
| 6,379,354 B1 * | 4/2002 | Rogozinski | ........ | A61B 17/6416 606/260 |
| 6,835,196 B2 * | 12/2004 | Biedermann | ...... | A61B 17/7032 606/308 |
| 8,366,746 B2 * | 2/2013 | Kiester | ................ | A61B 17/705 606/260 |
| 8,425,564 B2 * | 4/2013 | Kiester | ................ | A61B 17/705 606/260 |
| 8,882,803 B2 * | 11/2014 | Iott | ...................... | A61B 17/705 606/246 |
| 10,149,702 B2 * | 12/2018 | Ewer | ................... | A61B 17/7038 |
| 2003/0045874 A1 * | 3/2003 | Thomas, Jr. | ........ | A61B 17/7049 606/250 |
| 2006/0079895 A1 * | 4/2006 | McLeer | ............... | A61B 17/863 606/279 |
| 2007/0043365 A1 * | 2/2007 | Ritland | ................ | A61B 17/705 606/257 |
| 2007/0270820 A1 * | 11/2007 | Dickinson | ......... | A61B 17/7007 606/279 |
| 2009/0177232 A1 * | 7/2009 | Kiester | ................ | A61B 17/705 606/260 |
| 2010/0137913 A1 * | 6/2010 | Khatchadourian | ......................... | A61B 17/7083 606/258 |

(Continued)

*Primary Examiner* — Ellen C Hammond
(74) *Attorney, Agent, or Firm* — Bell & Manning, LLC

(57) ABSTRACT

A spinal rod extension system includes a rod portion of a spinal rod extension and a connector portion connected to the rod portion. The connector portion is configured for insertion through a screw head of an existing pedicle screw that is used to secure an existing spinal rod. The spinal rod extension system also includes a screw head connector configured to mount to the screw head of the existing pedicle screw to secure the connector portion to the existing spinal rod. The screw head connector includes a first end wall and a second end wall that are connected to one another by a pair of cross connectors.

12 Claims, 30 Drawing Sheets

(56) References Cited

U.S. PATENT DOCUMENTS

2010/0160981 A1* 6/2010 Butler ................. A61B 17/705
  606/308
2011/0270314 A1* 11/2011 Mueller ............... A61B 17/704
  606/264
2018/0317973 A1* 11/2018 Abbasi ............... A61B 17/7037

* cited by examiner

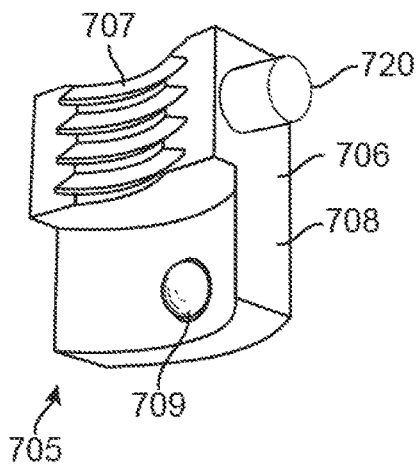
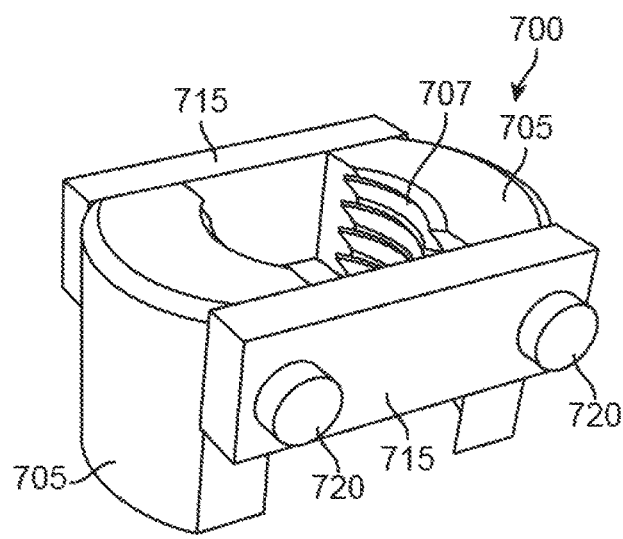
FIG. 21A   FIG. 21B
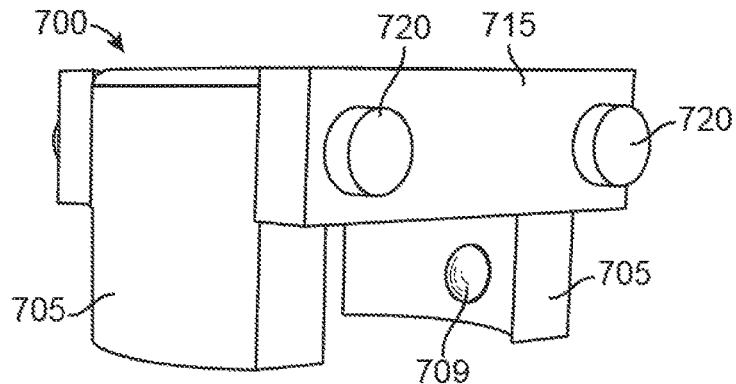
FIG. 21C
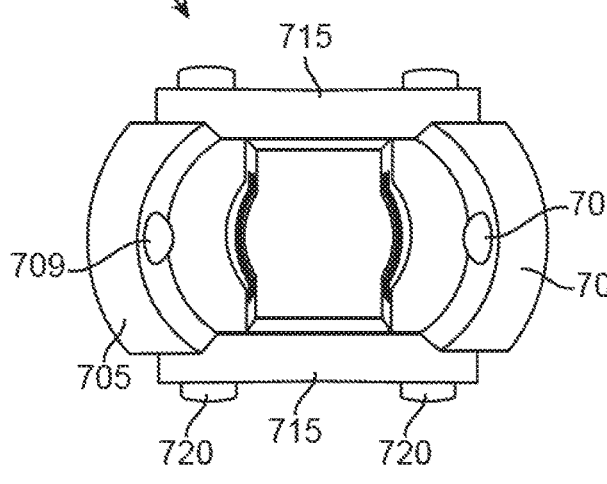
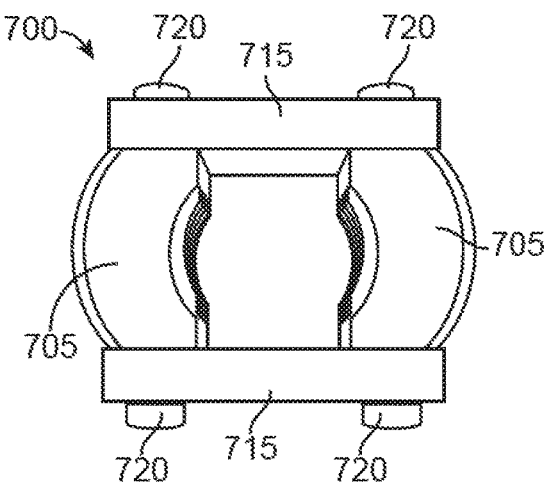
FIG. 21D   FIG. 21E

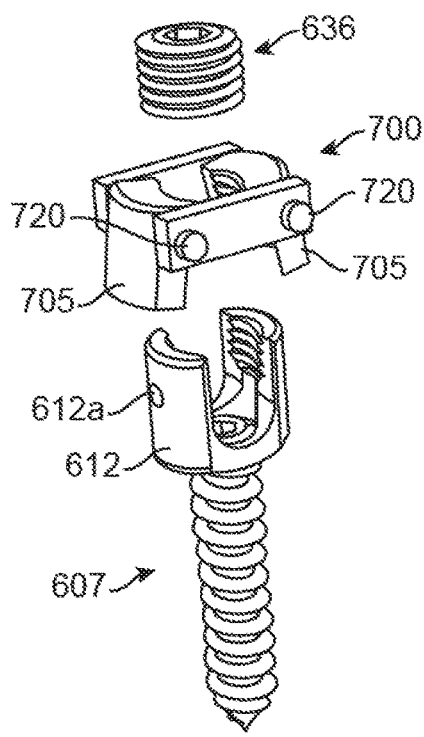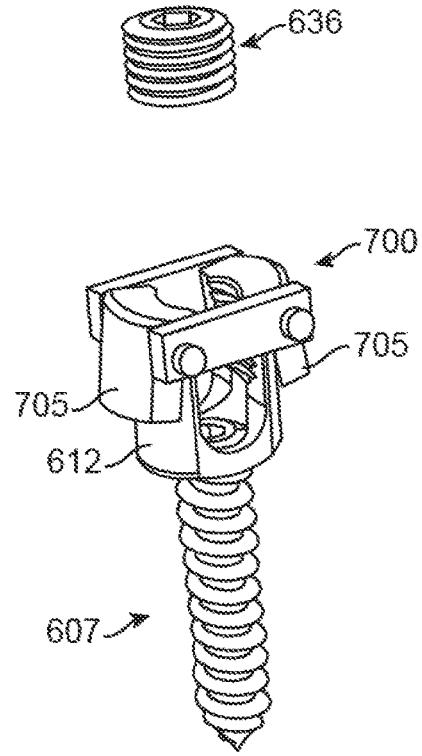
FIG. 22A  FIG. 22B
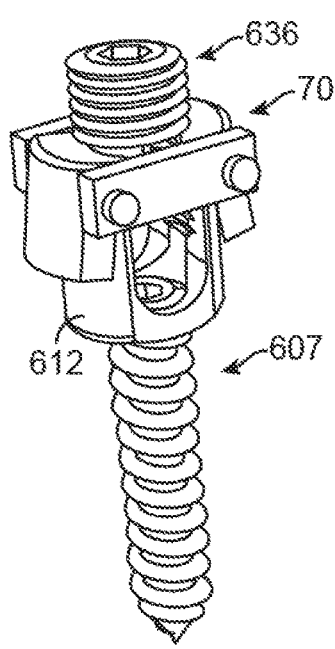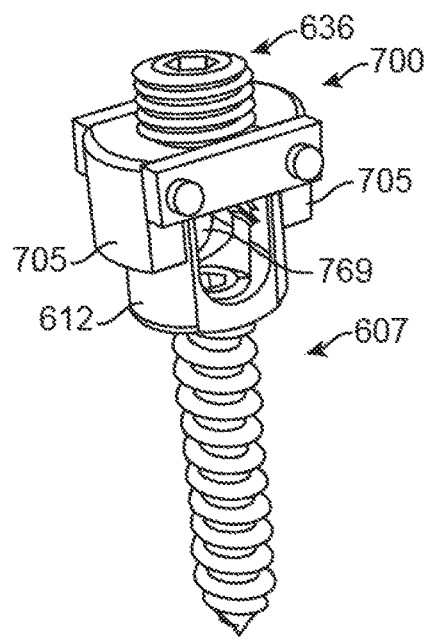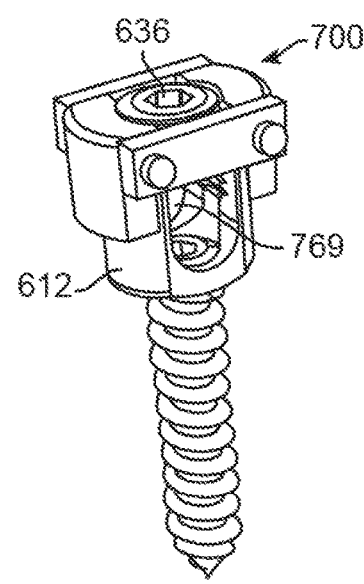
FIG. 22C  FIG. 22D  FIG. 22E

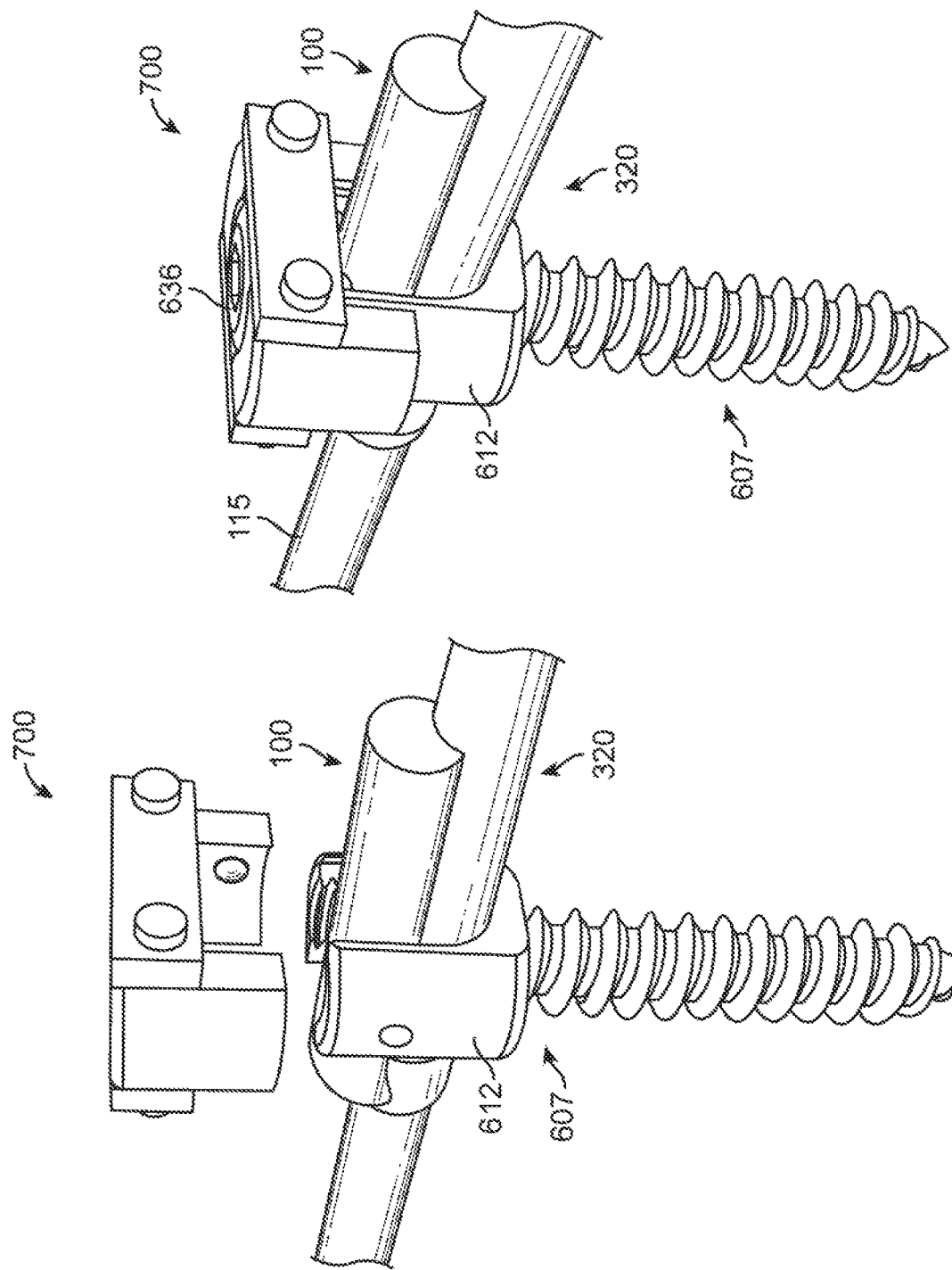

SPINAL ROD IMPLANT EXTENSION

CROSS-REFERENCE TO RELATED APPLICATIONS

The present application is a continuation-in-part application of U.S. patent application Ser. No. 15/250,394 filed on Aug. 29, 2016, which claims the priority benefit of U.S. Provisional App. No. 62/241,987 filed on Oct. 15, 2015, the entire disclosures of which are incorporated herein by reference.

BACKGROUND

A spinal rod is a metal cylinder implant used in spinal surgery to stabilize a vertebral segment. In a spinal fusion surgery, a spinal rod can be used to connect screws inserted into adjacent vertebral bodies in order to prevent motion and allow fusion to occur across adjacent spine segments. Rods are used extensively in spine fusion systems. After a patient has undergone an instrumented spinal fusion operation, on occasion they can later develop problems at the spinal levels above or below the fusion, necessitating another surgery, also called a revision surgery, with extension of the instrumentation. In so doing, one option is to remove the existing instrumentation and replace it with all new instrumentation, but this may involve an extensive surgery. Another option is to link in to the existing instrumentation, which may decrease the surgical morbidity for the patient, because the previously placed implants can be preserved.

SUMMARY

A spinal rod extension includes a rod portion, a connector portion, a lip, and a connector. The connector portion is mounted to the rod portion. The connector portion is configured for insertion through a screw head of an existing pedicle screw that is used to secure an existing spinal rod. The lip is mounted to the rod portion, and is configured to engage at least a portion of an end of the existing spinal rod. The connector is configured to secure the connector portion to the existing spinal rod.

A method of mounting a spinal rod extension includes accessing at least a portion of an existing spinal rod. The method also includes removing a locking cap from an existing pedicle screw that secures the existing spinal rod. The method also includes placing a connector portion of the spinal rod extension through a screw head of the existing pedicle screw. The method further includes using a connector to secure the connector portion to the existing spinal rod.

An illustrative spinal rod extension system includes a rod portion of a spinal rod extension and a connector portion connected to the rod portion. The connector portion is configured for insertion through a screw head of an existing pedicle screw that is used to secure an existing spinal rod. The spinal rod extension system also includes a screw head connector configured to mount to the screw head of the existing pedicle screw to secure the connector portion to the existing spinal rod. The screw head connector includes a first end wall and a second end wall that are connected to one another by a pair of cross connectors.

An illustrative screw head connector includes a first cross connector and a second cross connector. The screw head connector also includes a first end wall pivotally mounted to the first cross connector and the second cross connector. At least a portion of the first end wall includes first threads configured to match a threaded portion of a pedicle screw head. The screw head connector further includes a second end wall pivotally mounted to the first cross connector and the second cross connector. At least a portion of the second end wall includes second threads configured to match the threaded portion of the pedicle screw head.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

BRIEF DESCRIPTION OF THE DRAWINGS

FIG. 21A depicts an end wall of a pedicle screw head connector used to secure the spinal rod extension to an existing spinal rod via a connection with an existing pedicle screw head in accordance with an illustrative embodiment.

FIG. 21B is an angled top view of the pedicle screw head connector in accordance with an illustrative embodiment.

FIG. 21C is an angled perspective view of the pedicle screw head connector in accordance with an illustrative embodiment.

FIG. 21D is a bottom view of the pedicle screw head connector in accordance with an illustrative embodiment.

FIG. 21E is a top view of the pedicle screw head connector in accordance with an illustrative embodiment.

FIG. 22A depicts a pedicle screw head connector proximate to a pedicle screw in accordance with an illustrative embodiment.

FIG. 22B depicts the pedicle screw head connector placed over the pedicle screw head in accordance with an illustrative embodiment.

FIG. 22C depicts a set screw (locking cap) proximate to the pedicle screw head connector of FIG. 22B in accordance with an illustrative embodiment.

FIG. 22D depicts the set screw partially screwed into the pedicle screw head connector in accordance with an illustrative embodiment.

FIG. 22E depicts the set screw fully screwed into the pedicle screw head connector in accordance with an illustrative embodiment.

FIG. 24A is an angled view of a pedicle screw head connector adjacent to a rod extension positioned in a pedicle screw head in accordance with an illustrative embodiment.

FIG. 24B is an angled view of the pedicle screw head connector of FIG. 24A mounted to the pedicle screw head to secure the rod extension in accordance with an illustrative embodiment.

DETAILED DESCRIPTION

Spinal instrumentation is used to stabilize the spine for spinal fusion operations. Such spinal instrumentation can include a spinal rod which is secured to one or more vertebrae via pedicle screws. Adjacent segment deterioration can occur above or below an instrumented spinal fusion, necessitating more surgery and an overall longer spinal rod. Removing an existing spinal rod and replacing it with another, longer spinal rod is a highly invasive procedure. However, it can be difficult to link in to existing pedicle screw and spinal rod instrumentation, especially when the subsequent surgery is done in a minimally invasive manner through small incisions. Existing devices attempt to allow for minimally invasive spinal rod extensions, but all of the existing mechanisms are designed to bypass the existing pedicle screw heads at the top or bottom of a construct. This makes the connecting device bulky, which can lead to potential complications and/or patient discomfort.

Figure 1:
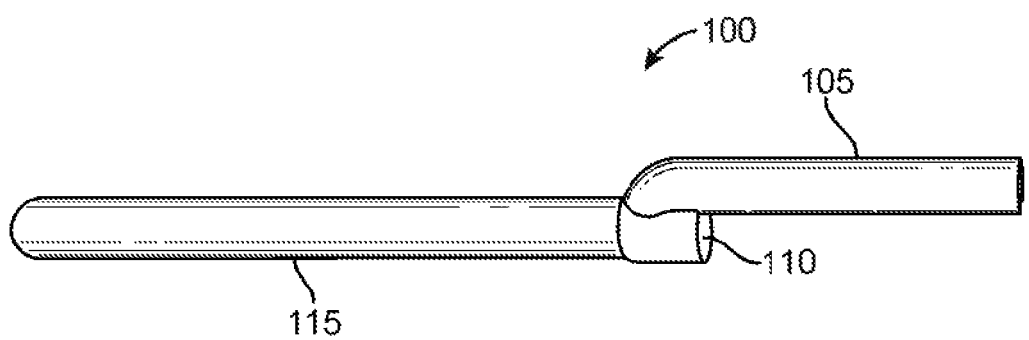
FIG. 1 is a side view of a spinal rod extension in accordance with an illustrative embodiment.

Described herein are spinal rod extensions that allow for minimally invasive surgery, while providing a low profile design that minimizes the bulk of the extension. Specifically, the spinal rod extensions described herein go through existing pedicle screw heads instead of bypassing them. FIG. 1 is a side view of a spinal rod extension 100 in accordance with an illustrative embodiment. The spinal rod extension is a single piece but has three main features or sections. Sections 105 and 110 are designed to attach to an existing spinal rod (not shown), and section 115 (also referred to herein as a rod portion) is the extended length of rod that will attach to new pedicle screws (not shown). Section 105 (also referred to herein as a connector portion) has a curved undersurface (not shown) that fits onto the top of an existing spinal rod (not shown), and section 110 comprises a lip or an opening that accommodates the end of an existing spinal rod, thus enabling mating of the spinal rod extension to an existing spinal rod. In an alternative embodiment, spinal rod extension 100 can be comprised of two or more pieces, with a hinge or other articulation connecting section 110 (which is a single unit with section 105) to section 115.

Figure 2:
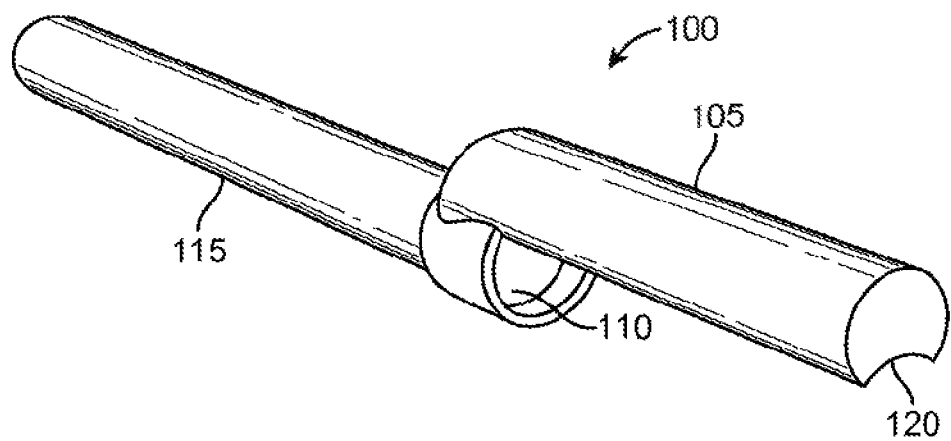
FIG. 2 is an angled view of a spinal rod extension in accordance with an illustrative embodiment.

FIG. 2 is an angled view of a spinal rod extension 100 in accordance with an illustrative embodiment. Section 105 has a curved undersurface 120 that fits onto the top of an existing spinal rod (not shown) and section 110 comprises an opening that accommodates the end of an existing spinal rod (not shown), thus enabling mating of the spinal rod extension to an existing spinal rod (not shown). Section 110 can partially or fully surround the existing spinal rod, depending on the implementation. Section 115 is the extended length of rod that will attach to new pedicle screws (not shown).

Figure 3:
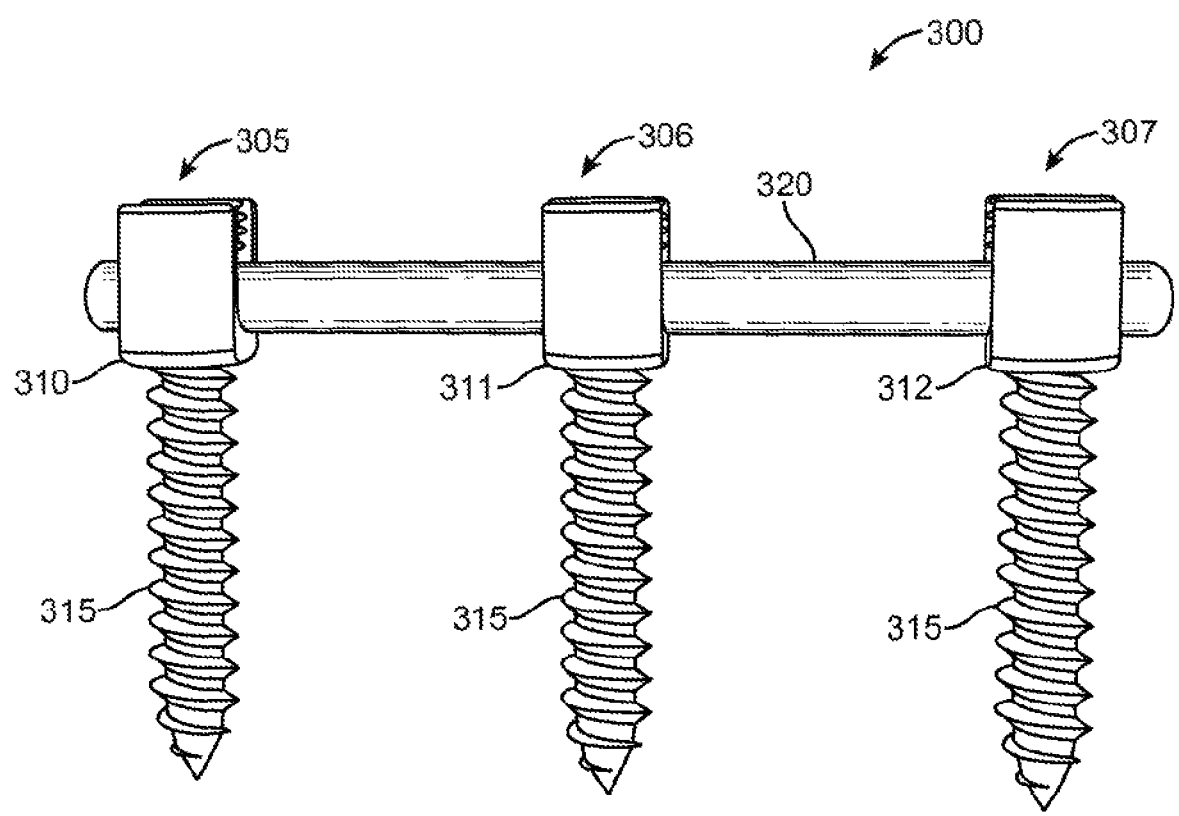
FIG. 3 is a side view of an existing spinal rod attached to three pedicle screws in accordance with an illustrative embodiment.

FIG. 3 is a side view of an existing two-level pedicle screw instrumentation construct 300, in accordance with an illustrative embodiment. The pedicle screw instrumentation construct depicted here would span two intervertebral disk levels while performing a two-level instrumented spinal fusion and includes an existing spinal rod 320 attached to three pedicle screws 305, 306, and 307. The pedicle screws 305, 306, and 307 are comprised of a threaded shaft 315 that in practice would be screwed into a vertebra of a patient (not shown) and a head 310, 311, and 312 that accommodates the existing spinal rod 320.

Figure 4:
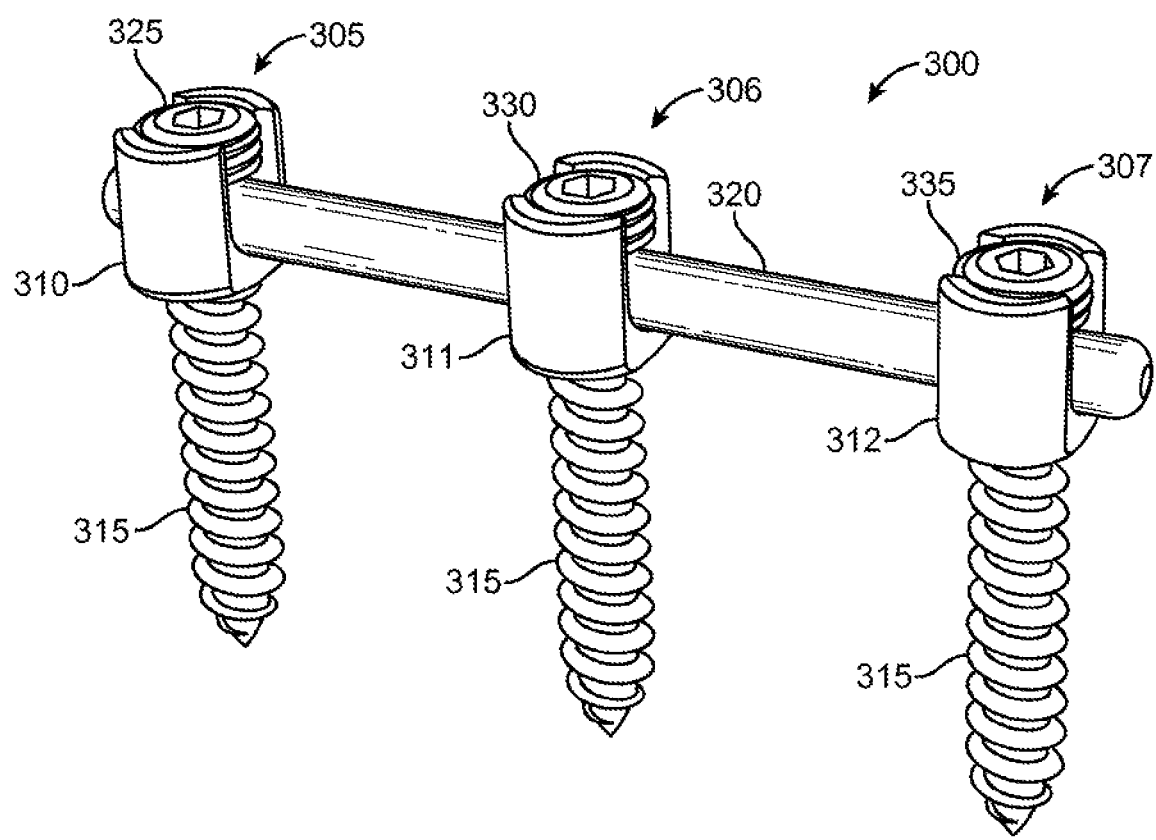
FIG. 4 is an angled view of an existing spinal rod attached to three pedicle screws in accordance with an illustrative embodiment.

FIG. 4 is an angled view of an existing two-level pedicle screw instrumentation construct 300, in accordance with an illustrative embodiment. The pedicle screw instrumentation construct depicted here would span two intervertebral disk levels while performing a two-level instrumented spinal fusion and includes an existing spinal rod 320 attached to three pedicle screws 305, 306, and 307. The pedicle screws are comprised of a threaded shaft 315 that would be screwed into a vertebra of a patient (not shown) and a u-shaped head 310, 311, and 312 that is configured to receive the existing spinal rod 320. Depending on the implementation, a u-shaped head 310, 311, and 312 may be pivotally mounted to the threaded shaft 315 of the pedicle screw. At least an upper portion of the u-shaped head 310, 311, and 312 is threaded and configured to receive a locking cap 325, 330, and 335. The locking cap may be alternatively referred to as a set screw. The existing spinal rod 320 is secured to the pedicle screws by locking caps (or alternatively called set screws) 325, 330, and 335. The locking caps 325, 330, and 335 are used to secure the existing spinal rod 320 such that it remains within the u-shaped head 310, 311, and 312 of the pedicle screw 305, 306, and 307.

Figure 5:
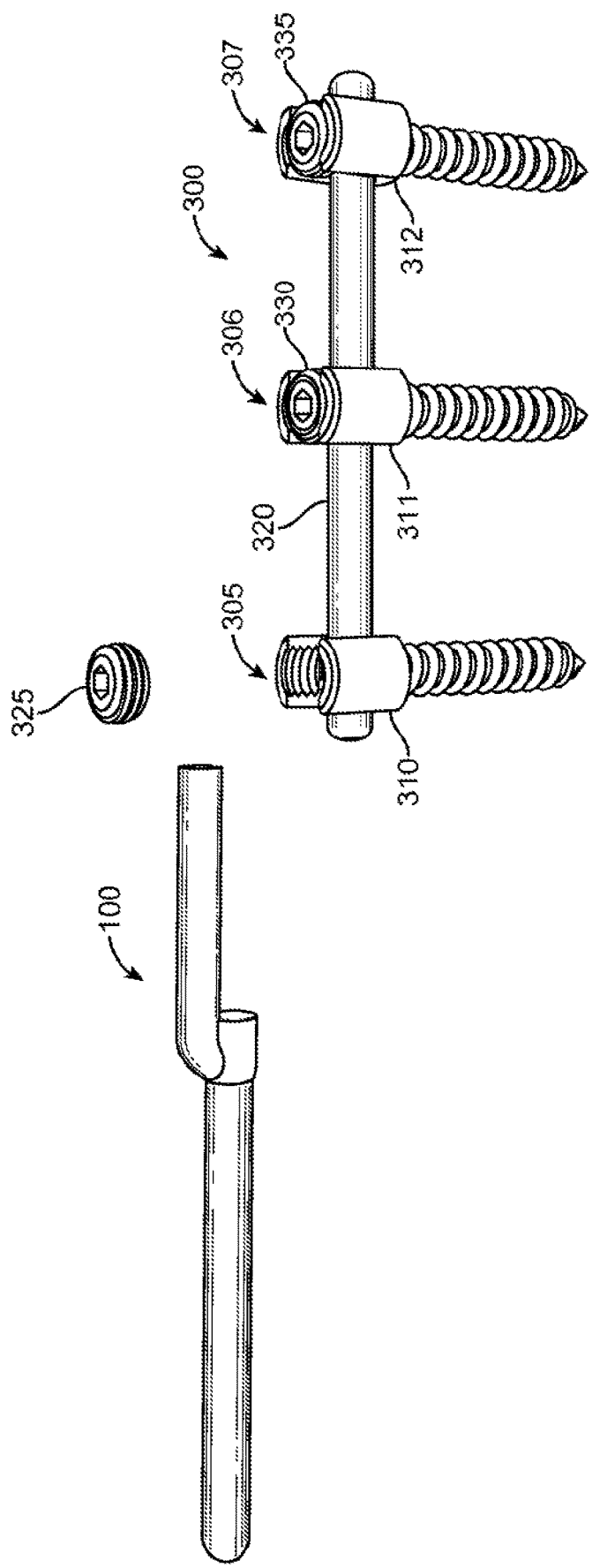
FIG. 5 is an angled view of a spinal rod extension and an existing spinal rod attached to two pedicle screws, with the locking cap of the third pedicle screw removed in anticipation of the spinal rod extension being mounted to the existing spinal rod, in accordance with an illustrative embodiment.

FIG. 5 is an angled view of a spinal rod extension 100 and an existing two-level pedicle screw instrumentation construct 300, in accordance with an illustrative embodiment. Locking cap 325 has been removed from pedicle screw head 310 of pedicle screw 305 in order to create space for the spinal rod extension 100 to mate to existing spinal rod 320. Pedicle screws 306 and 307 have the locking caps 330 and 335 still engaged to pedicle screw heads 311 and 312, thus continuing to attach to rod 320.

Figure 6:
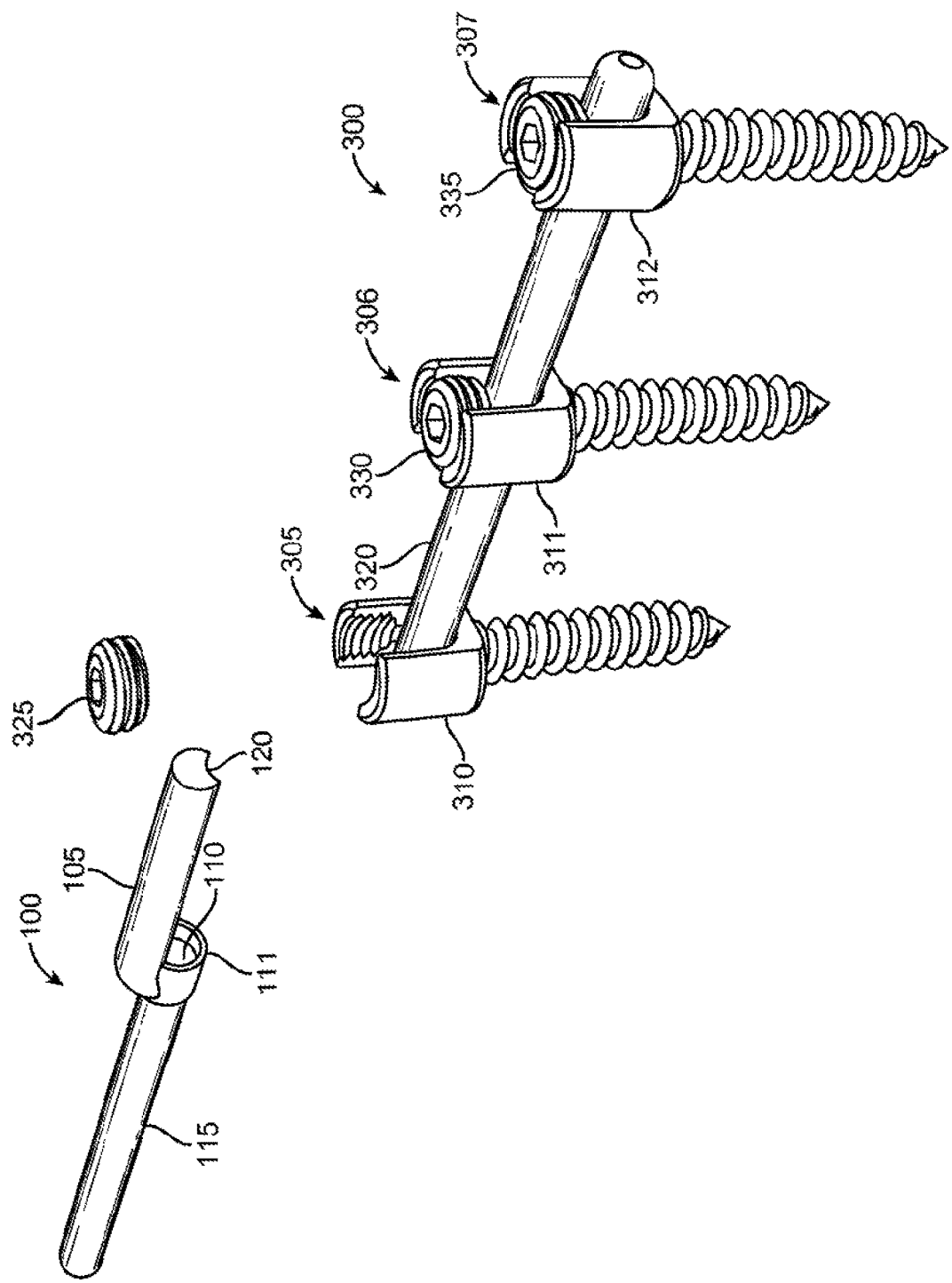
FIG. 6 is an angled view of a spinal rod extension, and an existing spinal rod attached to two pedicle screws, with the locking cap of the third pedicle screw removed in anticipation of the spinal rod extension being mounted to the existing spinal rod, in accordance with an illustrative embodiment.

FIG. 6 is an angled view of a spinal rod extension 100 and an existing two-level pedicle screw instrumentation construct 300, in accordance with an illustrative embodiment. Locking cap 325 has been removed from pedicle screw head 310 of pedicle screw 305 in order to create space for the spinal rod extension 100 to mate to existing spinal rod 320. Pedicle screws 306 and 307 have the locking caps 330 and 335 still engaged to pedicle screw heads 311 and 312, thus continuing to attach to rod 320.

The spinal rod extension 100 can be used to extend the existing spinal rod 320 in the event that the patient with the existing spinal rod 320 needs additional surgery to correct and/or fuse one or more adjacent vertebrae. The spinal rod extension 100 includes a connector portion comprised of an opening 110 which is configured to mate with at least a portion of the terminal end of the existing spinal rod 320 and a section 105 that rests on top of the existing spinal rod and fits intimately by virtue of a concave undersurface 120 that mates with the convex surface of existing spinal rod 320. The spinal rod extension 100 also includes a rod portion 115 that can be used to lengthen the existing spinal rod 320. In an illustrative embodiment, the rod portion 115 and the connector portions 105 and 110 can be molded together or manufactured as a single piece with the rod portion 115 and the connector portions 105 and 110 having various lengths. In an alternative embodiment, the rod portion 115 may be detachably mounted to the connector portion 110. In such an embodiment, prior to or during surgery, the surgeon can select a rod portion 115 of appropriate length and mount it to the connector portion 110. The mounting can be performed via one or more of a fastener, clamp(s), male/female connection, etc. In another embodiment, the rod portion 115 may articulate relative to the connector portion 110.

In use, the set screw 325 is removed such that the connector portion 105 of the spinal rod extension 100 can be inserted through the u-shaped head 310 of the pedicle screw 305 that was used in the original surgery to secure the existing spinal rod 320. In an illustrative embodiment, a bottom portion (in accordance with the orientation depicted in FIG. 2) of the connector portion 105 can be curved or concave such that the connector portion 105 form-fits the convex contour of the existing spinal rod 320. As such, when mounted to the existing spinal rod 320, the connector portion 105 can be flush with or within a top edge of the u-shaped head 310. In an alternative embodiment, the connector portion 105 may extend slightly beyond the top edge of the u-shaped head 310.

In at least some embodiments, the spinal rod extension 100 includes an opening 110 with a lip 111 that is configured to mate with at least a portion of the terminal end of the existing spinal rod 320 and help secure the spinal rod extension 100 to the existing spinal rod 320. In one embodiment, the lip 111 can be configured to engage just a bottom portion of the existing spinal rod 320 that extends past the u-shaped head 310 of the pedicle screw 305. Alternatively, the lip 111 can form a circular (i.e., rod-shaped) opening 110 that is configured to receive the entire end of the existing spinal rod 320 that extends past the u-shaped head 310 of the pedicle screw 305 and form a male/female connection between the existing spinal rod 320 and the spinal rod extension 100.

Figure 7:
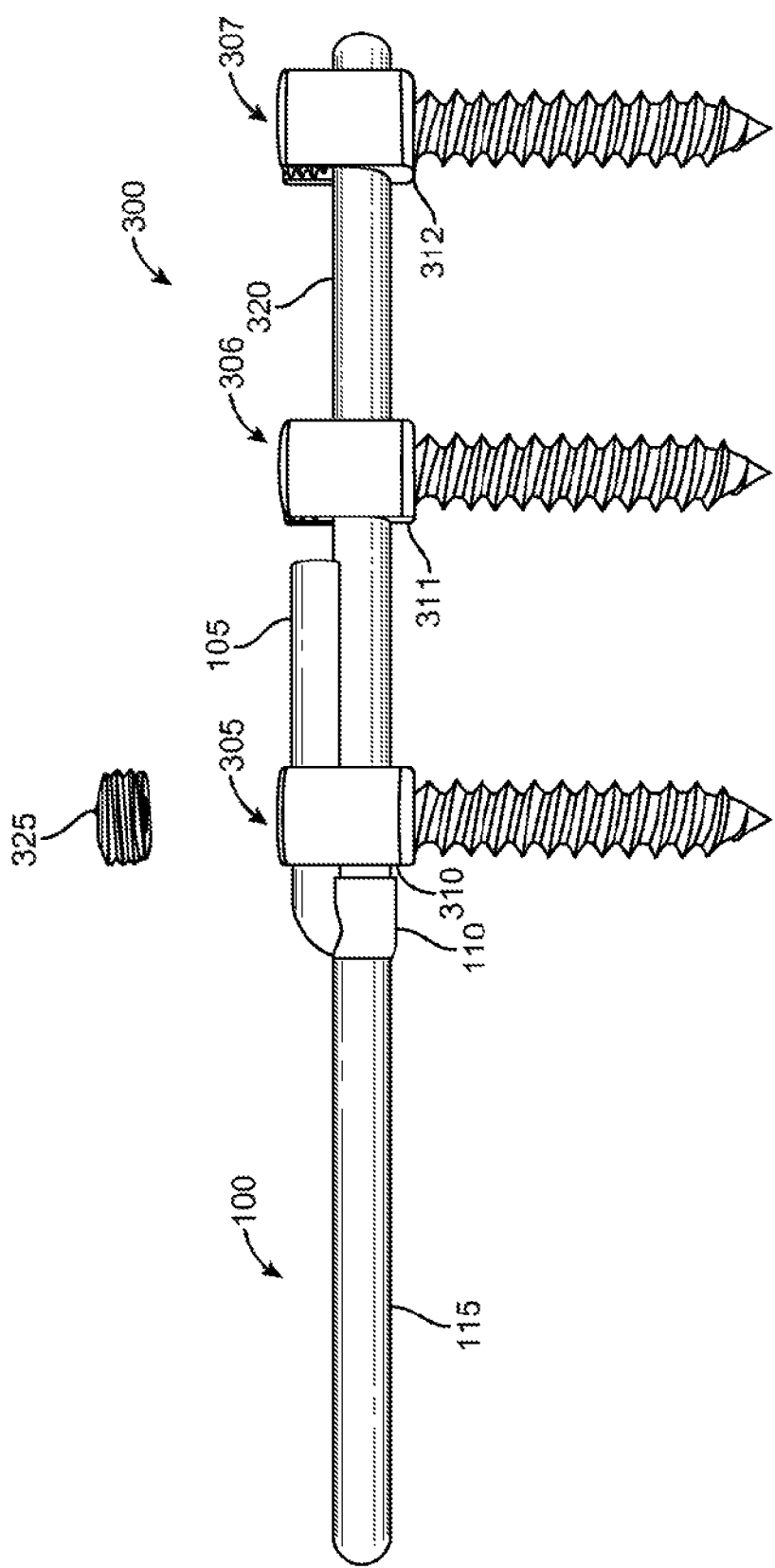
FIG. 7 is a side view of a spinal rod extension, and an existing spinal rod attached to two pedicle screws, with the locking cap of the third pedicle screw removed and the spinal rod extension mounted on the existing spinal rod, in accordance with an illustrative embodiment.

FIG. 7 is a side view of a spinal rod extension 100 mated to an existing spinal rod 320 of an existing two-level pedicle screw instrumentation construct 300, in accordance with an illustrative embodiment. Locking cap 325 has been removed from pedicle screw head 310 of pedicle screw 305, and section 105 of spinal rod extension 100 passes through screw head 310 in the region previously occupied by locking cap 325 and is seated on existing spinal rod 320. Section 110 of spinal rod extension 100 fits around the end of existing spinal rod 320 in a male-female connection configuration, and the extension section 115 of spinal rod extension 100 is available to be secured to new pedicle screws (not shown). Pedicle screws 306 and 307 have the locking caps still engaged to pedicle screw heads 311 and 312, thus continuing to attach to the existing spinal rod 320.

Figure 8:
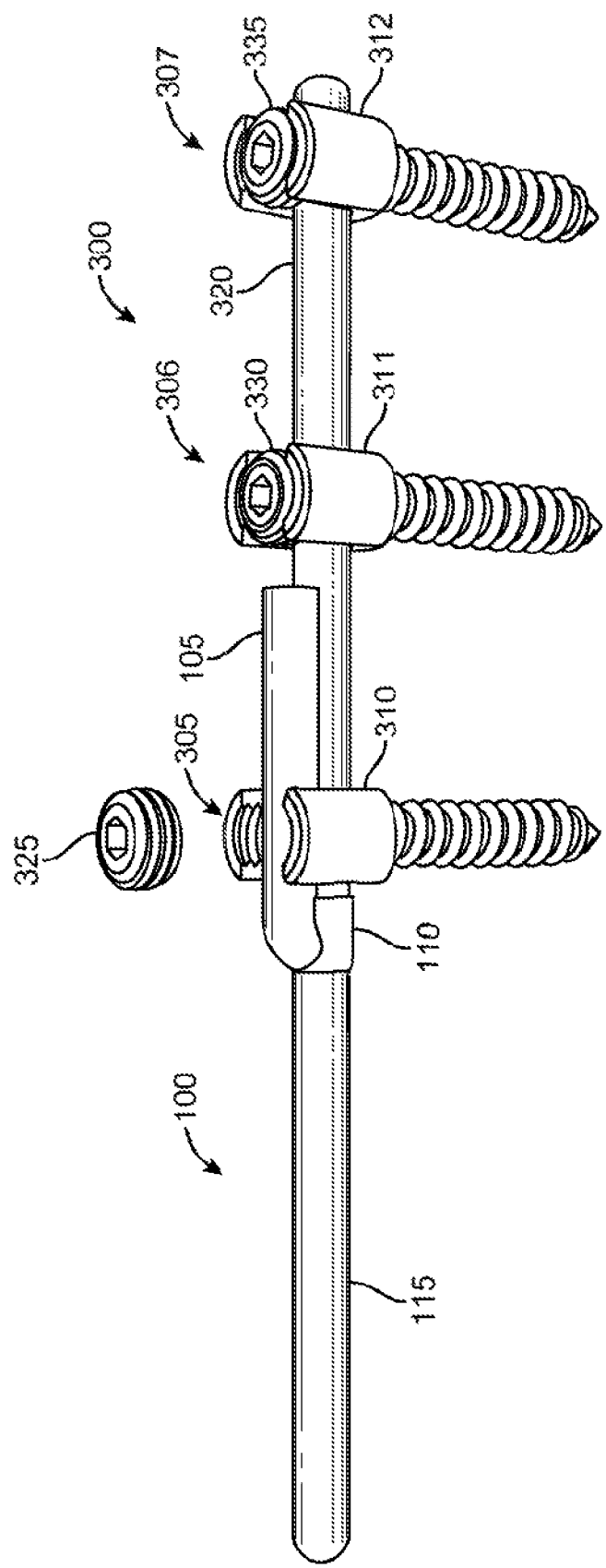
FIG. 8 is an angled view of a spinal rod extension, and an existing spinal rod attached to two pedicle screws, with the locking cap of the third pedicle screw removed and the spinal rod extension mounted on the existing spinal rod, in accordance with an illustrative embodiment.

FIG. 8 is an angled view of a spinal rod extension 100 mated to an existing spinal rod 320 of an existing two-level pedicle screw instrumentation construct 300, in accordance with an illustrative embodiment. Locking cap 325 has been removed from pedicle screw head 310 of pedicle screw 305, and section 105 of spinal rod extension 100 passes through screw head 310 in the region previously occupied by locking cap 325 and is seated on existing spinal rod 320. Section 110 of spinal rod extension 100 fits around the end of existing spinal rod 320, and the extension section 115 of spinal rod extension 100 is available to be secured to new pedicle screws (not shown). Pedicle screws 306 and 307 have the locking caps 330 and 335 still engaged to pedicle screw heads 311 and 312, thus continuing to attach pedicle screws 306 and 307 to the existing spinal rod 320.

Figure 9:
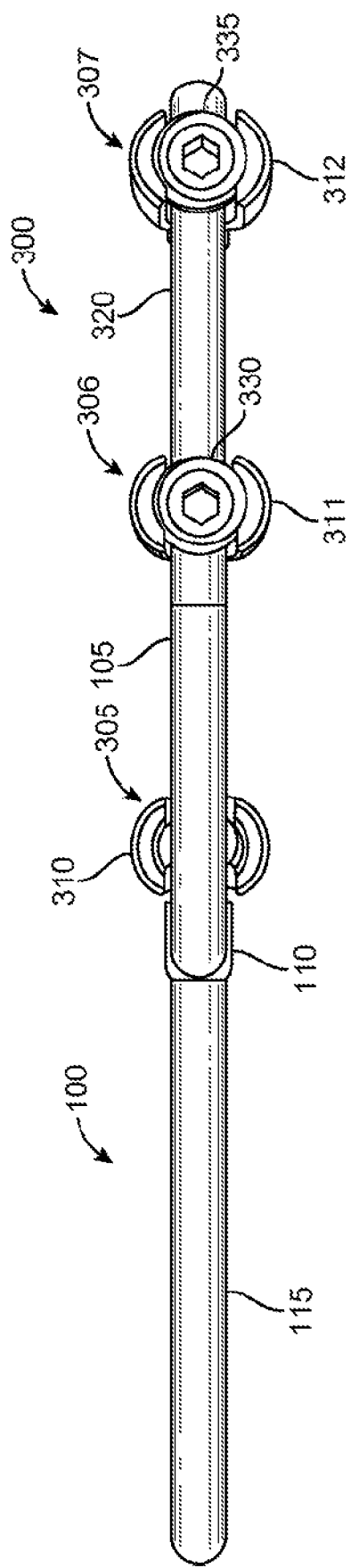
FIG. 9 is a top view of a spinal rod extension, and an existing spinal rod attached to two pedicle screws, with the locking cap of the third pedicle screw removed and the spinal rod extension mounted on the existing spinal rod, in accordance with an illustrative embodiment.

FIG. 9 is a top view of a spinal rod extension 100 mated to an existing spinal rod 320 of an existing two-level pedicle screw instrumentation construct 300, in accordance with an illustrative embodiment. Locking cap 325 (shown in FIG. 8 but no longer shown in FIG. 9) has been removed from pedicle screw head 310 of pedicle screw 305, and section 105 of spinal rod extension 100 passes through screw head 310 in the region previously occupied by locking cap 325 and is seated on existing spinal rod 320. Section 110 of spinal rod extension 100 fits around the end of existing spinal rod 320, and the extension section 115 of spinal rod extension 100 is available to be secured to new pedicle screws (not shown). Pedicle screws 306 and 307 have the locking caps 330 and 335 still engaged to pedicle screw heads 311 and 312, thus continuing to attach pedicle screws 306 and 307 to the existing spinal rod 320.

Figure 10:
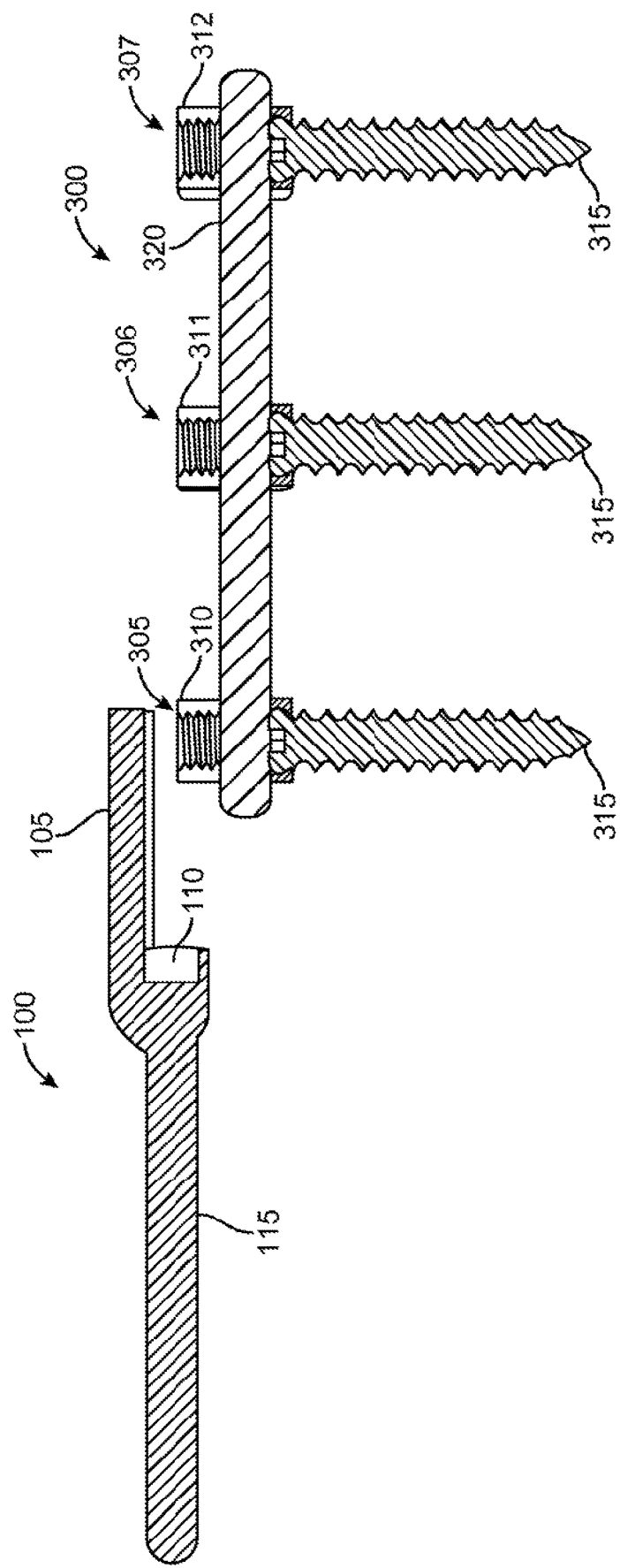
FIG. 10 is a cross sectional view of a spinal rod extension, and an existing spinal rod along with three pedicle screws, in anticipation of the spinal rod extension being mounted on the existing spinal rod, in accordance with an illustrative embodiment.

FIG. 10 is a cross-sectional side view of a spinal rod extension 100 and an existing spinal rod 320 of an existing two-level pedicle screw instrumentation construct 300, in accordance with an illustrative embodiment. Section 110 of spinal rod extension 100 fits around the end of existing spinal rod 320, and the extension section 115 of spinal rod extension 100 is available to be secured to new pedicle screws (not shown). Pedicle screws 306 and 307 would have the locking caps 330 and 335 (shown in FIG. 8, not shown here) still engaged to pedicle screw heads 311 and 312, thus continuing to attach pedicle screws 306 and 307 to the existing spinal rod 320. The threaded shafts 315 of the pedicle screws 305, 306, and 307 are shown. Locking cap 325 (shown in FIG. 8 but no longer shown in FIG. 10) has been removed from pedicle screw head 310 of pedicle screw 305, and section 105 of spinal rod extension 100 passes through screw head 310 in the region previously occupied by locking cap 325 and is seated on existing spinal rod 320.

Figure 11:
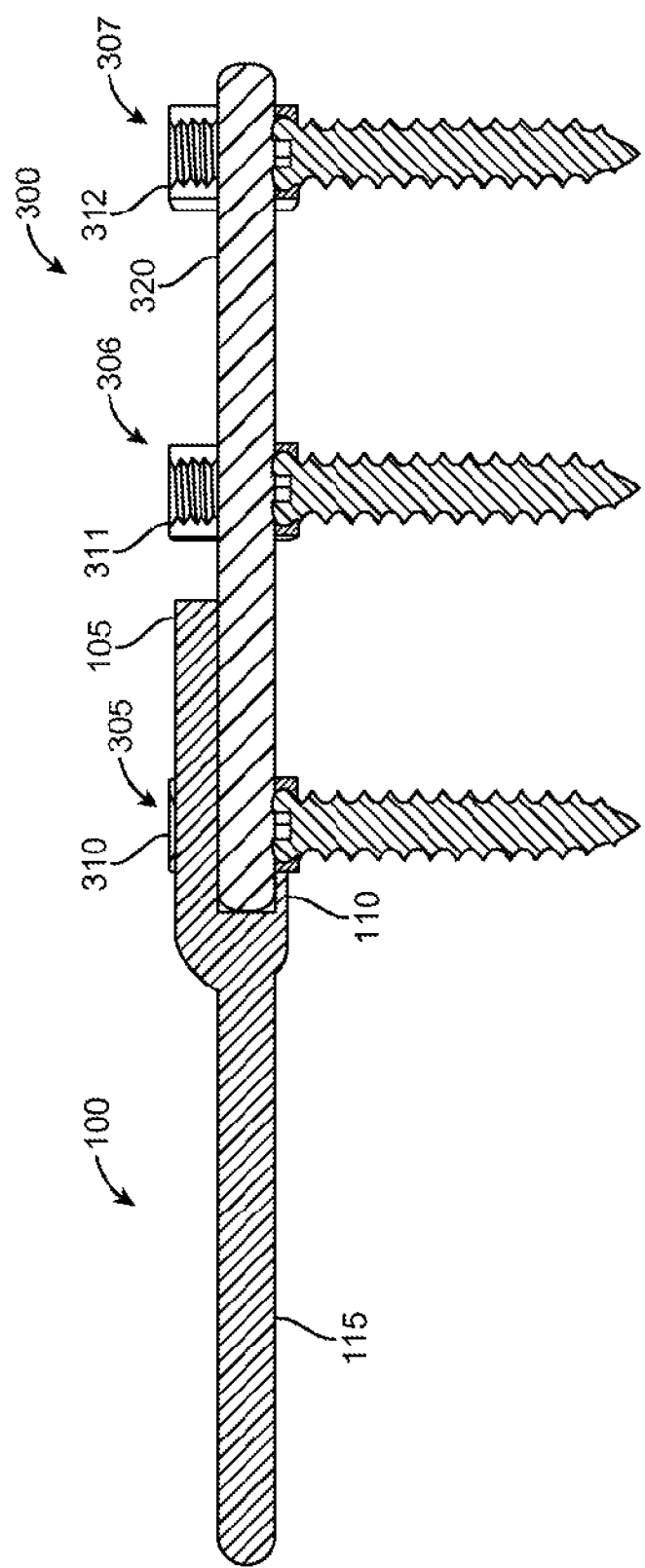
FIG. 11 is a cross sectional view of a spinal rod extension, and an existing spinal rod along with three pedicle screws, with the spinal rod extension mounted on the existing spinal rod, in accordance with an illustrative embodiment.

FIG. 11 is a cross-sectional side view of a spinal rod extension 100 mated to an existing spinal rod 320 of an existing two-level pedicle screw instrumentation construct 300, in accordance with an illustrative embodiment. Section 110 of spinal rod extension 100 fits around the end of existing spinal rod 320, and the extension section 115 of spinal rod extension 100 is available to be secured to new pedicle screws (not shown). Locking cap 325 (shown in FIG. 8 but no longer shown here) has been removed from pedicle screw head 310 of pedicle screw 305, and section 105 of spinal rod extension 100 passes through screw head 310 in the region previously occupied by locking cap 325 and is seated on existing spinal rod 320. Pedicle screws 306 and 307 would have the locking caps 330 and 335 (shown in FIG. 8, not shown here) still engaged to pedicle screw heads 311 and 312, thus continuing to attach pedicle screws 306 and 307 to the existing spinal rod 320.

Figure 12:
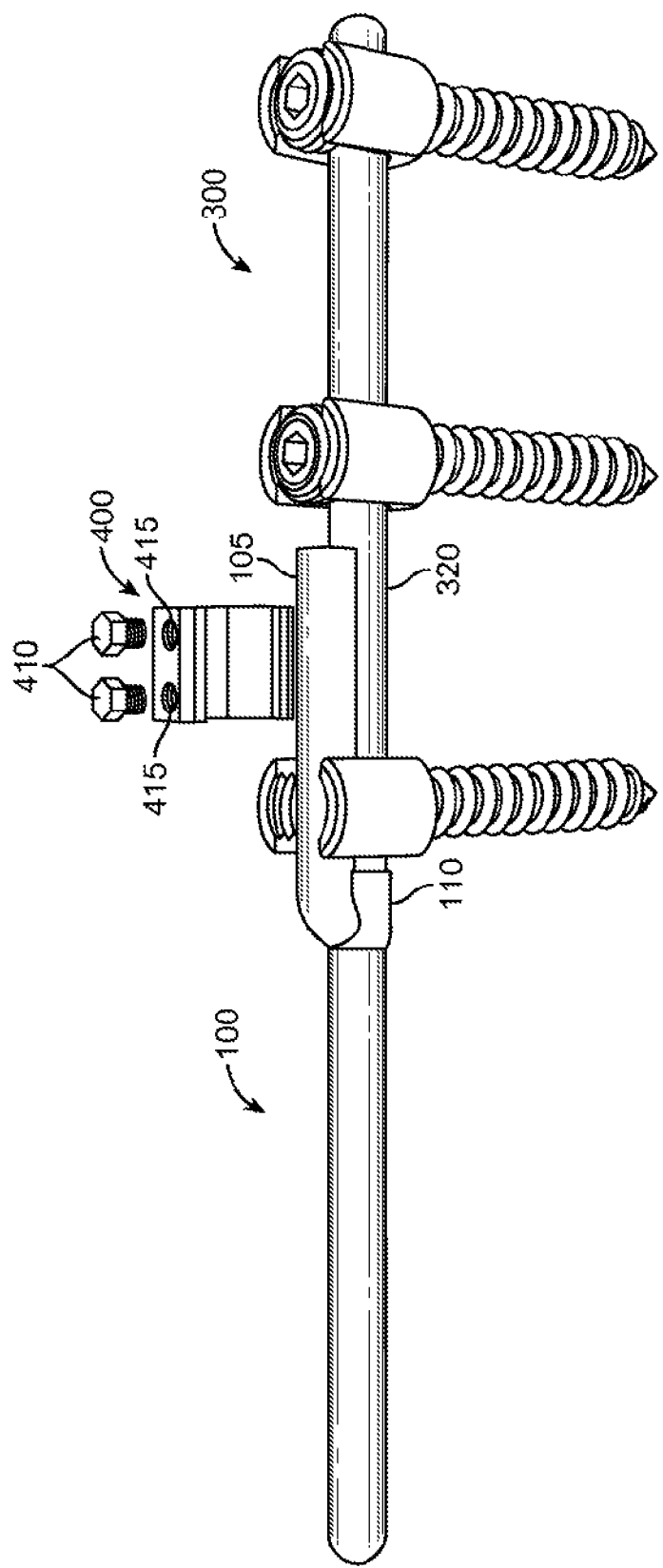
FIG. 12 is an angled view of a spinal rod extension mounted on an existing spinal rod, in anticipation of a clamp being applied to secure the spinal rod extension to the existing spinal rod, in accordance with an illustrative embodiment.

FIG. 12 is an angled view of a spinal rod extension 100 mated to an existing spinal rod 320 of an existing two-level pedicle screw instrumentation construct, as also seen in FIG. 8, in this figure prepared to be secured by a clamp 400, in accordance with an illustrative embodiment. The clamp 400 can be any type of circular clamp known to those of skill in the art. In one embodiment, the clamp 400 can be a C-shaped partial ring with one side open such that the clamp could be slipped around both the connector portion 105 and the existing rod 320 from the side and then secured with one or more bolt(s) or screw(s) 410. In another embodiment, the clamp 400 can be a ring-shape that has a hinge on one side and a latch on the other side so that the clamp 400 is able to slide around the connector portion 105 and the existing rod 320 and then be latched into a closed position, thus securing the connector portion 105 to the existing rod 320. Another embodiment of the clamp 400 would be to use a strong woven fiber tape which could pass around both the connector portion 105 and the existing rod 320, and then be tied together or otherwise secured. Yet another embodiment of the clamp 400 can be a circular hose clamp that can be loosened and tightened via a screwdriver or other tool.

Clamp 400 is prepared to secure the spinal rod section 105 and its other sections comprising spinal rod extension 100 in its entirety to the existing spinal rod 320. Once the clamp is positioned around the spinal rod extension and existing spinal rod, it will be tightened via bolts or set screws 410 which screw into threaded holes 415 and press against rod extension section 105, thus securing spinal rod extension 100 to the existing spinal rod 320. The bolts or set screws 410 can be tightened such that ends of the bolts or set screws contact the top surface of the spinal rod extension section 105, thereby causing a fiction fit between the connector portion 105 and the existing spinal rod 320. The friction fit is maintained by the opening 110 and/or lip 111 (111 not shown) and the relationship of the concave undersurface of rod extension connector portion 105 to the convex surface of existing rod 320 and the clamp 400. In an alternative embodiment, the set screws 410 can be placed through threaded holes created in the rod extension section 105 itself, and create a frictional fit with existing rod 320.

One or more clamps may be used. In an alternative embodiment, more than one clamp may be used. In another alternative embodiment, the clamp may be smaller or larger and may use one bolt or may use three or more bolts to secure the clamp(s) to the rods. In another alternative embodiment, clamp 400 may be of any style or configuration that results in spinal rod extension 100 being secured to existing spinal rod 320.

Figure 13:
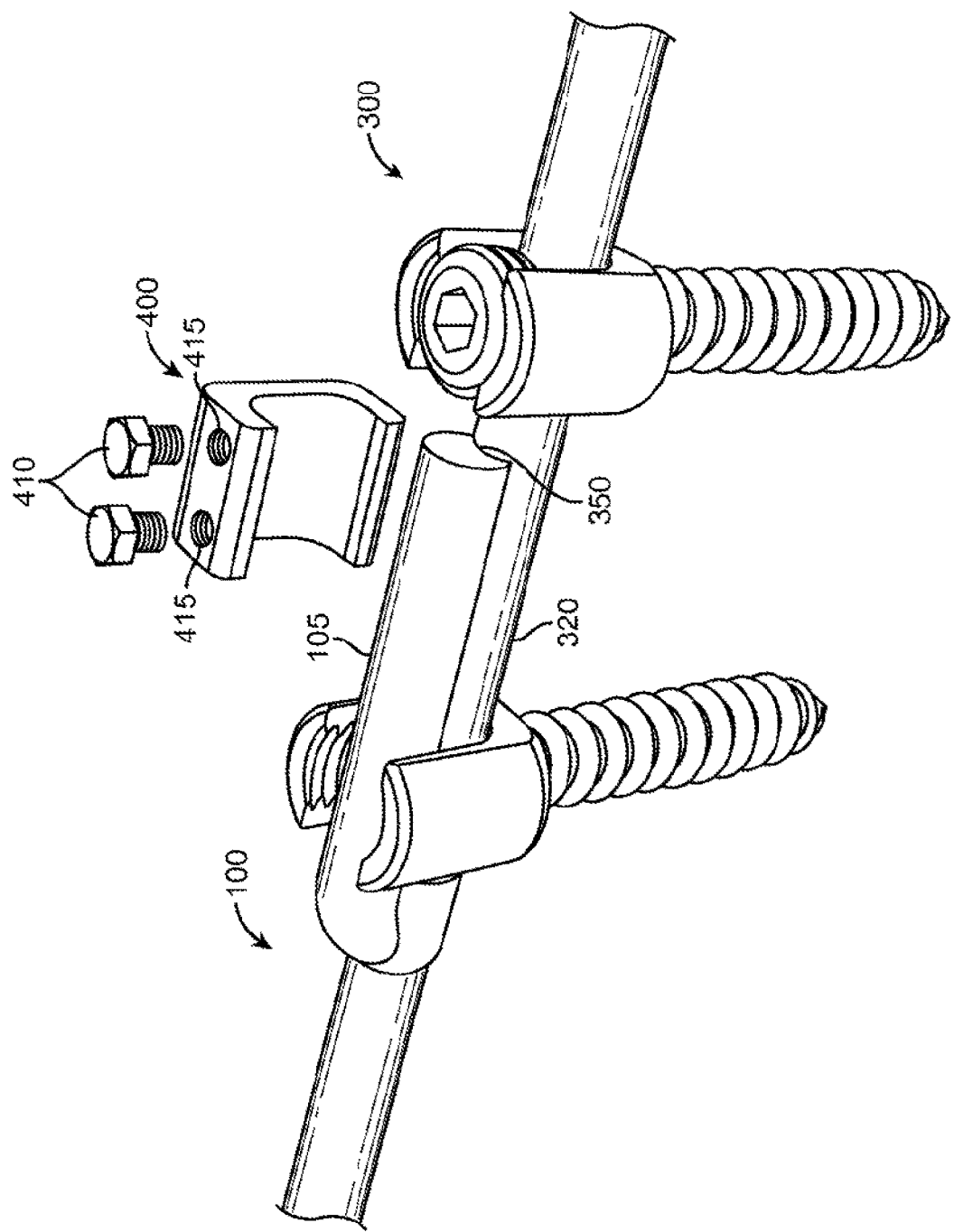
FIG. 13 is an angled close-up view of the area of connection of a spinal rod extension mounted to an existing spinal rod, in anticipation of a clamp being applied to secure the spinal rod extension to the existing spinal rod, in accordance with an illustrative embodiment.

FIG. 13 is an angled close-up view of a portion of spinal rod extension 100 mated to an existing spinal rod 320 of an existing two-level pedicle screw instrumentation construct, as also seen in FIG. 8 and FIG. 12, in accordance with an illustrative embodiment. Clamp 400 is prepared to secure the spinal extension rod section 105 and its other sections comprising spinal rod extension 100 in its entirety to the existing spinal rod 320. Once the clamp is positioned around the spinal rod extension and existing spinal rod, it will be tightened via bolts 410 which screw into threaded holes 415 and press against rod extension section 105, thus securing spinal rod extension 100 to the existing spinal rod 320. The curved concave undersurface of spinal rod extension section 105 is shown 350 to mate to the concave surface of existing spinal rod 320.

Figure 14:
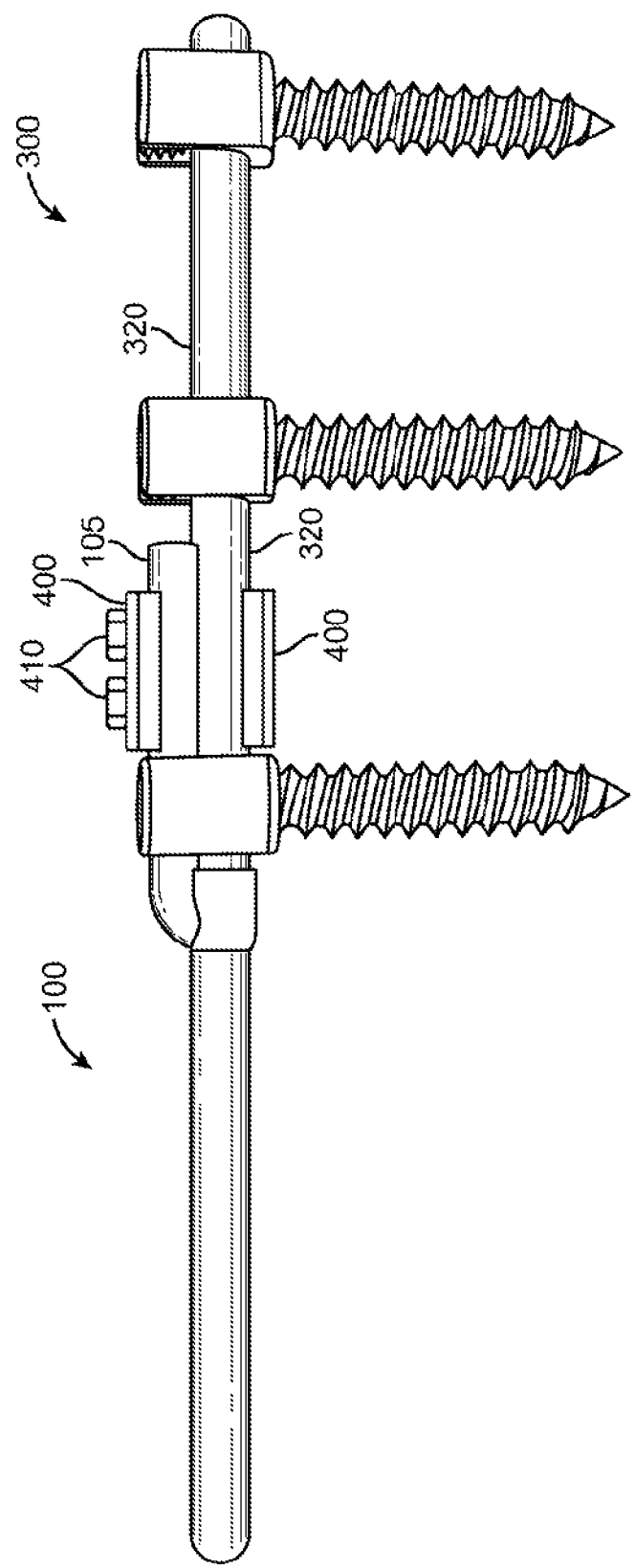
FIG. 14 is a side view of a spinal rod extension mounted on an existing spinal rod, with a clamp securing the spinal rod extension to the existing spinal rod, in accordance with an illustrative embodiment.

FIG. 14 is a side view of a spinal rod extension 100 mated to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320.

Figure 15:
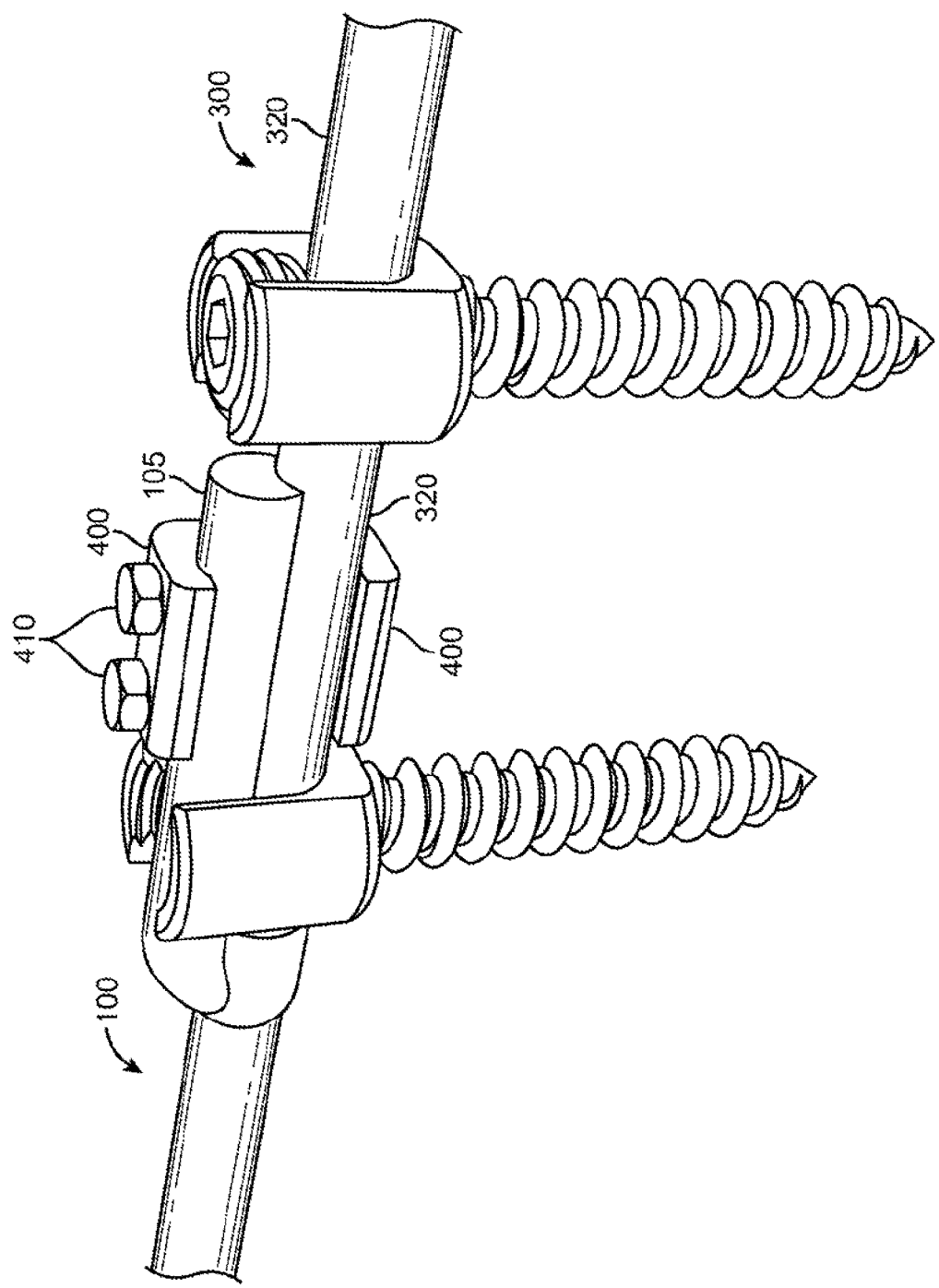
FIG. 15 is an angled close-up view of a spinal rod extension mounted on an existing spinal rod, with a clamp securing the spinal rod extension to the existing spinal rod, in accordance with an illustrative embodiment.

FIG. 15 is an angled close-up view of a spinal rod extension 100 mated to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320.

Figure 16:
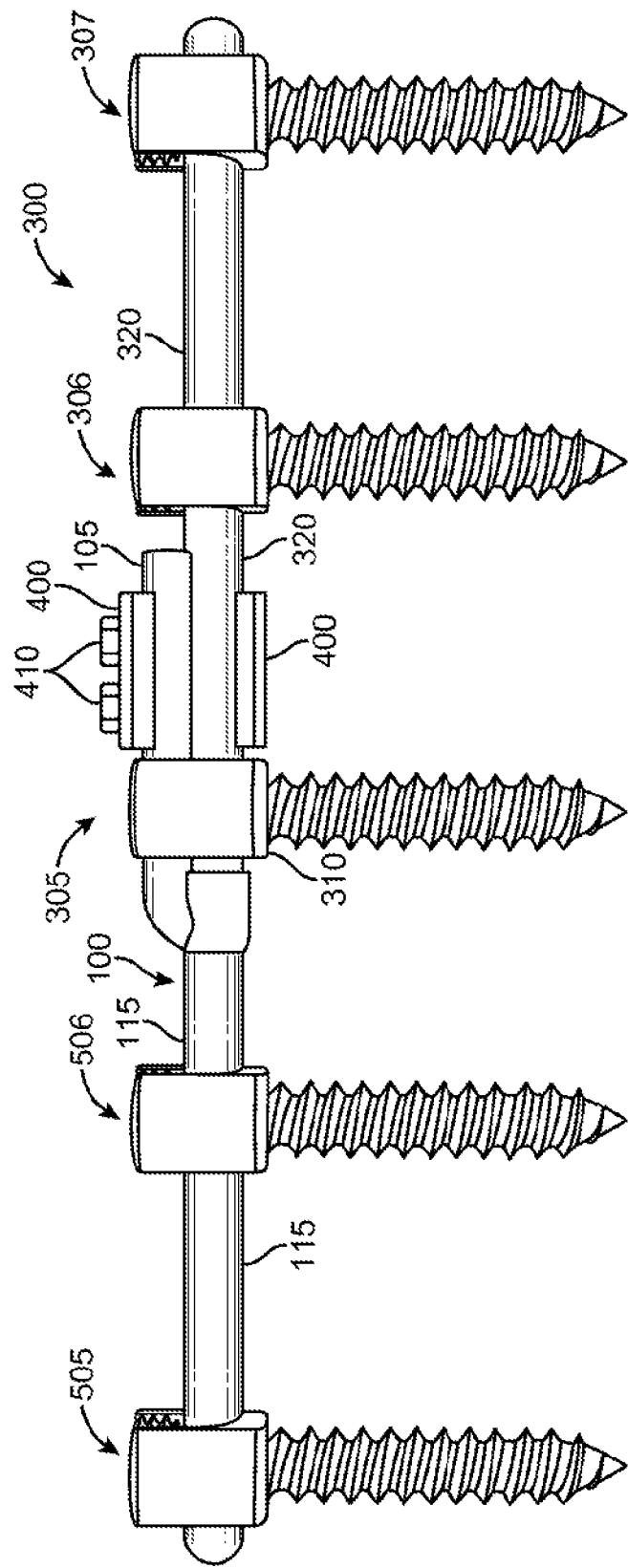
FIG. 16 is a side view of a spinal rod extension mounted on an existing spinal rod, with a clamp securing the spinal rod extension to the existing spinal rod, in accordance with an illustrative embodiment. The existing spinal rod is secured to two pedicle screws with locking caps, the spinal rod extension is now secured to two pedicle screws with locking caps, and both the spinal rod extension and the existing spinal rod are seated in the central pedicle screw head but are not attached to this pedicle screw with a locking cap.

FIG. 16 is a side view of a spinal rod extension 100 attached to new pedicle screws 505 and 506 and secured via clamp 400 to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320. Existing pedicle screws 306 and 307 are secured via locking caps to existing spinal rod 320, the locking cap has been removed from pedicle screw 305 so that section 105 can pass through the pedicle screw head 310, and new pedicle screws 505 and 506 are secured via locking caps to spinal rod extension section 115, thus allowing for extension of an existing spinal instrumentation construct to a new level or levels. In this embodiment, existing spinal instrumentation is a two-level construct and the rod extension attaches to two new levels. In practice, the existing spinal instrumentation may be two or more levels and the extension can be attached to one or more new levels as clinically indicated. The spinal rod extension can be made in different lengths to accommodate different length constructs.

Figure 17:
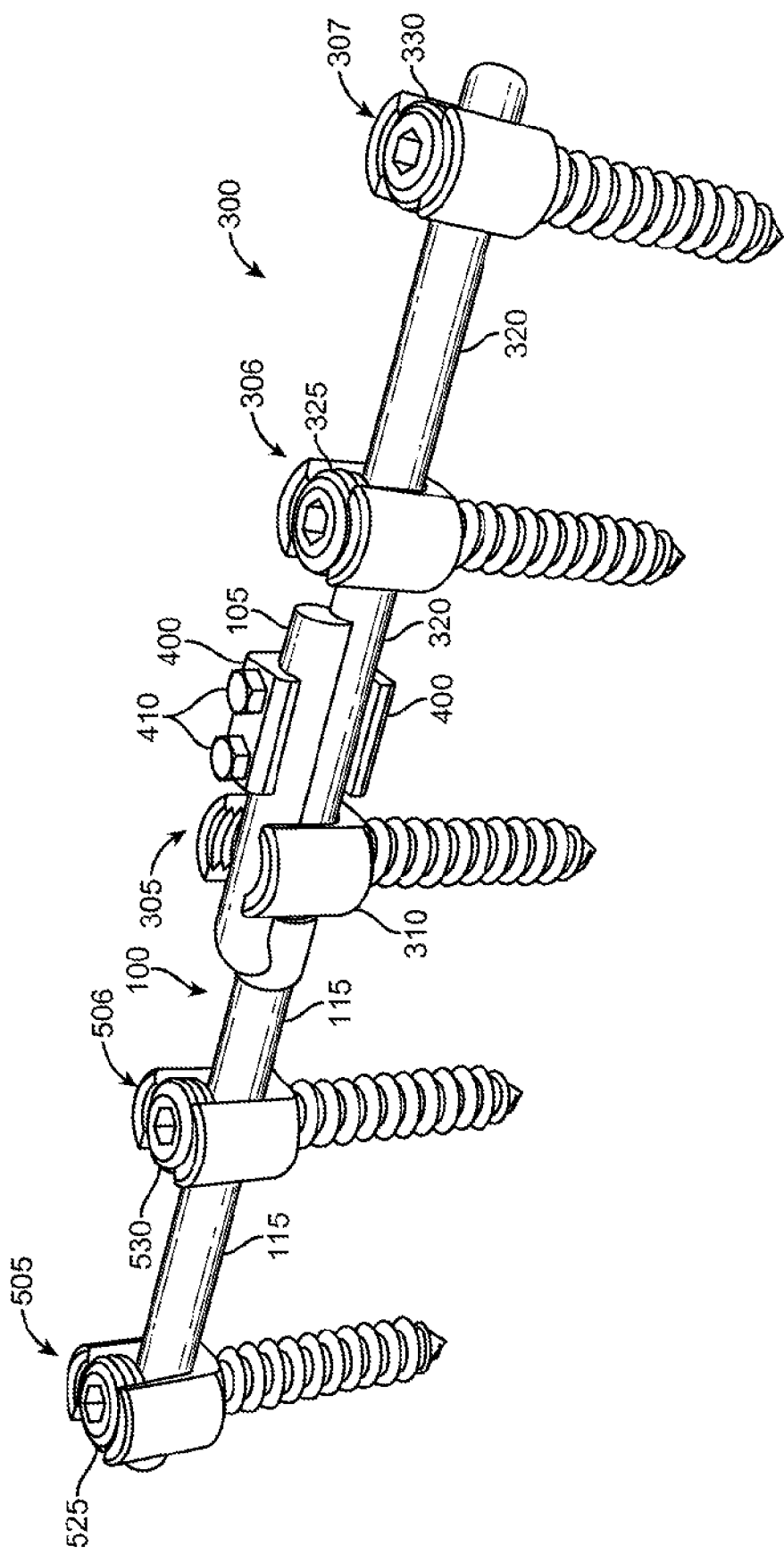
FIG. 17 is an angled view of a spinal rod extension mounted on an existing spinal rod, with a clamp securing the spinal rod extension to the existing spinal rod, in accordance with an illustrative embodiment. The existing spinal rod is secured to two pedicle screws with locking caps, the spinal rod extension is now secured to two pedicle screws with locking caps, and both the spinal rod extension and the existing spinal rod are seated in the central pedicle screw head but are not attached to this pedicle screw with a locking cap.

FIG. 17 is an angled view of a spinal rod extension 100 attached to new pedicle screws 505 and 506 and secured via clamp 400 to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320. Existing pedicle screws 306 and 307 are secured via locking caps 325 and 330 to existing spinal rod 320, and new pedicle screws 505 and 506 are secured via locking caps 525 and 530 to spinal rod extension section 115, thus allowing for extension of an existing spinal instrumentation construct to a new level or levels. The spinal rod extension passes through pedicle screw head 310 of pedicle screw 305, with the locking cap that originally was present in screw head 310 having been permanently removed. In an alternative embodiment, locking cap 325 could be removed from pedicle screw head 311 of pedicle screw 306 and a longer section 105 of spinal rod extension 100 could pass through both screw heads 310 and 311 and the spinal rod extension secured to the existing spinal rod in one or more places with one or more clamps. In the embodiment shown in FIG. 17, the existing spinal instrumentation is a two-level construct spanning two intervertebral disk spaces and the spinal rod extension attaches to two new levels. In practice, the existing spinal instrumentation may be two or more levels and the spinal rod extension can be attached to one or more new levels as clinically indicated. The spinal rod extension can be made in different lengths to accommodate different length constructs.

Figure 18:
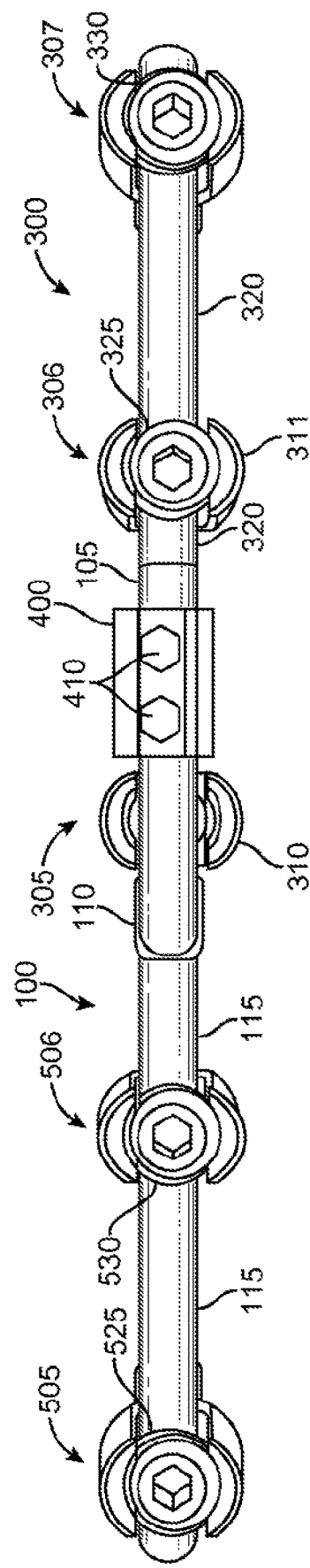
FIG. 18 is a top view of a spinal rod extension mounted on an existing spinal rod, with a clamp securing the spinal rod extension to the existing spinal rod, in accordance with an illustrative embodiment. The existing spinal rod is secured to two pedicle screws with locking caps, the spinal rod extension is now secured to two pedicle screws with locking caps, and both the spinal rod extension and the existing spinal rod are seated in the central pedicle screw head but are not attached to this pedicle screw with a locking cap.

FIG. 18 is a top view of a spinal rod extension 100 attached to new pedicle screws 505 and 506 and secured via clamp 400 to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320. Existing pedicle screws 306 and 307 are secured via locking caps 325 and 330 to existing spinal rod 320, and new pedicle screws 505 and 506 are secured via locking caps 525 and 530 to spinal rod extension section 115, thus allowing for extension of an existing spinal instrumentation construct to a new level or levels. The spinal rod extension passes through pedicle screw head 310 of pedicle screw 305, with the locking cap that originally was present in screw head 310 having been permanently removed. In an alternative embodiment, locking cap 325 could be removed from pedicle screw head 311 of pedicle screw 306 and a longer section 105 of spinal rod extension 100 could pass through both screw heads 310 and 311 and the spinal rod extension secured to the existing spinal rod in one or more places with one or more clamps. In an alternative embodiment, section 105 of spinal rod extension 100 can pass through more than two existing pedicle screw heads. In the embodiment shown in FIG. 18, the existing spinal instrumentation is a two-level construct spanning two intervertebral disk spaces and the spinal rod extension attaches to two new vertebral levels via pedicle screws. In practice, the existing spinal instrumentation may be two or more levels and the spinal rod extension can be attached to one or more new levels as clinically indicated. The spinal rod extension can be made in different lengths to accommodate different length constructs.

As discussed above with reference to FIG. 18, the spinal rod extension passes through pedicle screw head 310 of pedicle screw 305, with the locking cap that originally was present in screw head 310 having been permanently removed. In an alternative embodiment, the locking cap that was originally present in screw head 310 may be temporarily removed to accommodate the spinal rod extension. Upon placement of the spinal rod extension, the locking cap can be reinserted into the screw head 310 and used to secure or help secure the existing spinal rod.

Figure 19:
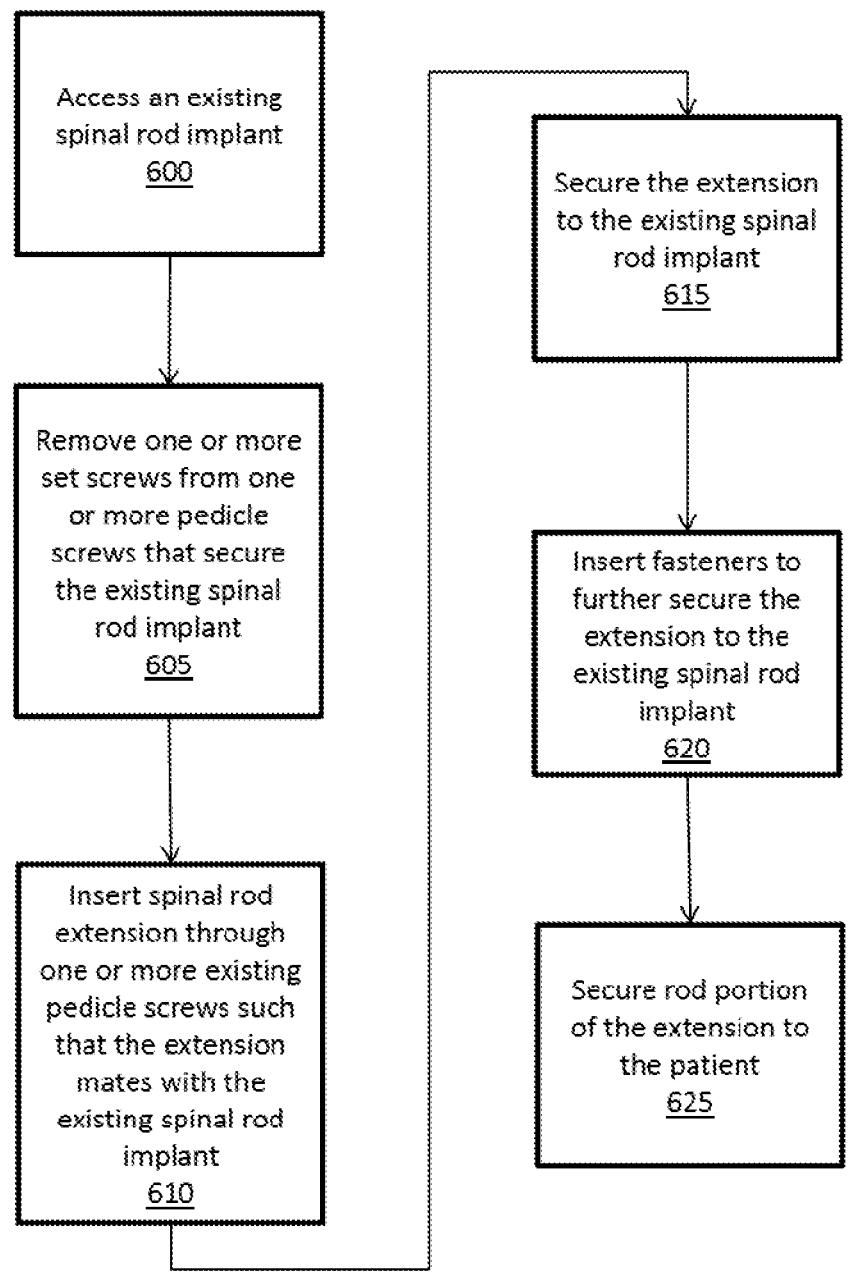
FIG. 19 is a flow diagram depicting a process for mounting a spinal rod extension to an existing spinal rod in accordance with an illustrative embodiment.

FIG. 19 is a flow diagram depicting a process for mounting a spinal rod extension to an existing spinal rod in accordance with an illustrative embodiment. In alternative embodiments, fewer, additional, and/or different operations may be performed. Additionally, the use of a flow diagram is not meant to be limiting with respect to the order of operations performed. In an operation 600, the surgeon accesses an existing spinal rod implant in a patient. Specifically, the surgeon can surgically approach the top or the bottom of the existing spinal rod and terminal pedicle screw, depending on where the spinal rod extension is to be placed.

In an operation 605, the surgeon removes one or more set screws (or locking caps) from one or more pedicle screws that secure the existing spinal rod. Upon removal of the one or more set screws, the existing spinal rod is exposed. In an operation 610, the surgeon inserts the spinal rod extension through the one or more existing pedicle screws from which the one or more set screws were removed. Specifically, the spinal rod extension is placed dorsally onto the existing spinal rod, passing through the pedicle screw u-shaped head(s) from with the set screw(s) have been removed. In an illustrative embodiment, the spinal rod extension is positioned so that a lip or opening of the spinal rod extension engages an end of the existing spinal rod that extends past a terminal pedicle screw that was used to secure the existing spinal rod.

In an operation 615, the spinal rod extension is secured to the existing spinal rod implant. In an illustrative embodiment, the spinal rod extension is secured to the existing spinal rod with one or more clamps. In alternative embodiments, a different securing method may be used. In an operation 620, the surgeon inserts fasteners to further secure the spinal rod extension to the existing spinal rod.

In an operation 625, the surgeon secures the rod portion of the spinal rod extension to the patient. In an illustrative embodiment, the spinal rod extension is attached to new pedicle screws that are placed cephalad or caudal to the existing spinal rod, depending on the needs of the patient. The rod portion of the spinal rod extension can be tunneled beneath the skin, subcutaneous tissues, and muscle of the patient in order to attach to the new pedicle screws that have been placed percutaneously. Alternatively, the rod portion of the spinal rod implant can be attached to new pedicle screws that have been placed through a conventional open posterior approach.

Figure 20A:
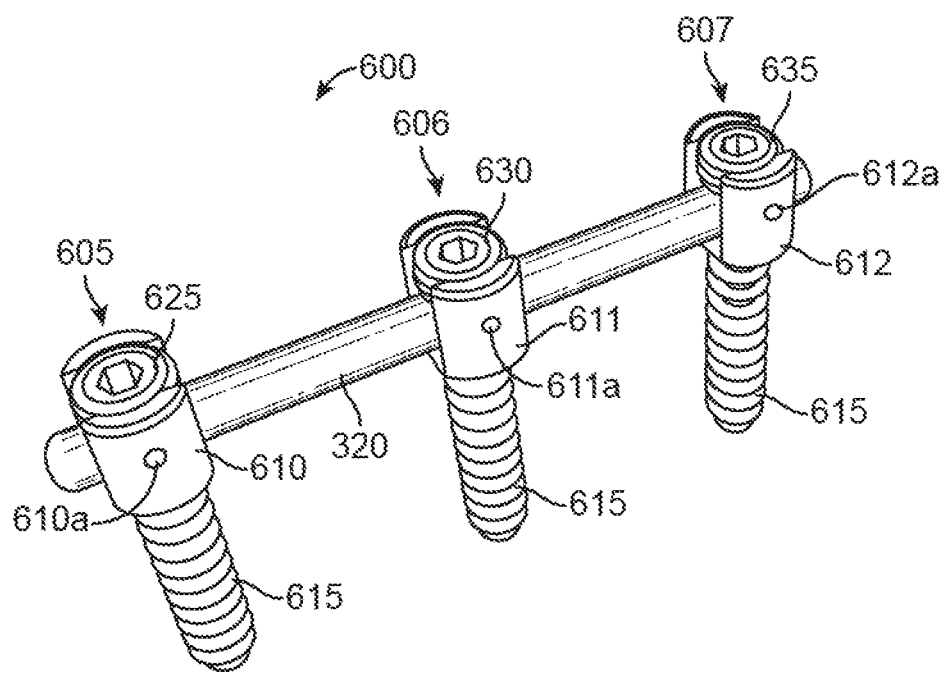
FIG. 20A depicts an existing spinal rod attached to three pedicle screws, in accordance with an illustrative embodiment.

FIG. 20A is an angled top view of an existing two-level pedicle screw instrumentation construct 600, in accordance with an illustrative embodiment. The pedicle screw instrumentation construct 600 depicted here would span two intervertebral disk levels while performing a two-level instrumented spinal fusion and includes an existing spinal rod 320 attached to three pedicle screws 605, 606, and 607. The pedicle screws include a threaded shaft 615 that is screwed into a vertebra of a patient (not shown) and a u-shaped pedicle screw head 610, 611, and 612 that is configured to receive a spinal rod 320. Depending on the implementation, the u-shaped pedicle screw heads 610, 611, and 612 may be pivotally mounted to the threaded shaft 615 of the pedicle screw. At least an upper portion of the u-shaped pedicle screw heads 610, 611, and 612 is threaded and configured to receive a locking cap 625, 630, and 635. The locking cap may be alternatively referred to as a set screw. The existing spinal rod 320 is secured to the pedicle screws by locking caps (or set screws) 625, 630, and 635. The set screws 625, 630, and 635 are used to secure the existing spinal rod 320 within the u-shaped pedicle screw heads 610, 611, and 612 of the pedicle screws 605, 606, and 607. Pedicle screw heads 610, 611, and 612 contain a surface feature 610a, 611a, 612a of variable shape. In the depicted embodiment, the surface features 610a, 611a, and 612a are in the form of a semi-spherical void or indentation designed to allow instruments to be reversibly and temporarily attached to the pedicle screw head. Alternatively, the surface feature can be square, rectangular, triangular, etc. in shape, and may be in the form of an indentation or a protrusion. The surface features 610a, 611a, and 612a create a connection point for instruments which are typically used for pedicle screw insertion and/or reduction of the rod into the pedicle screw head during a surgery, after which the instrument(s) is/are detached from the pedicle screw head.

Figure 20B:
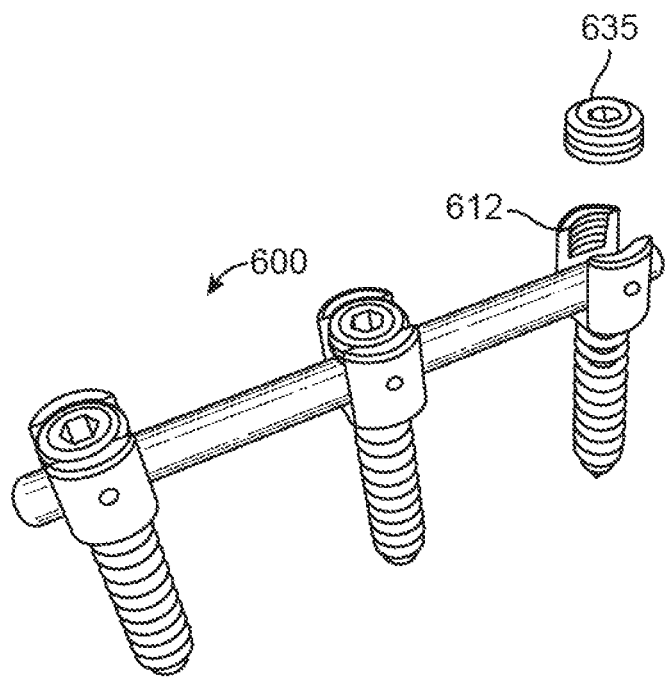
FIG. 20B depicts the existing spinal rod of FIG. 20A with a locking cap (set screw) removed from a third pedicle screw in accordance with an illustrative embodiment.

FIG. 20B is an angled top view of the existing two-level pedicle screw instrumentation construct 600 depicted in FIG. 20A, with set screw 635 now removed from screw head 612, in accordance with an illustrative embodiment.

Figure 20C:
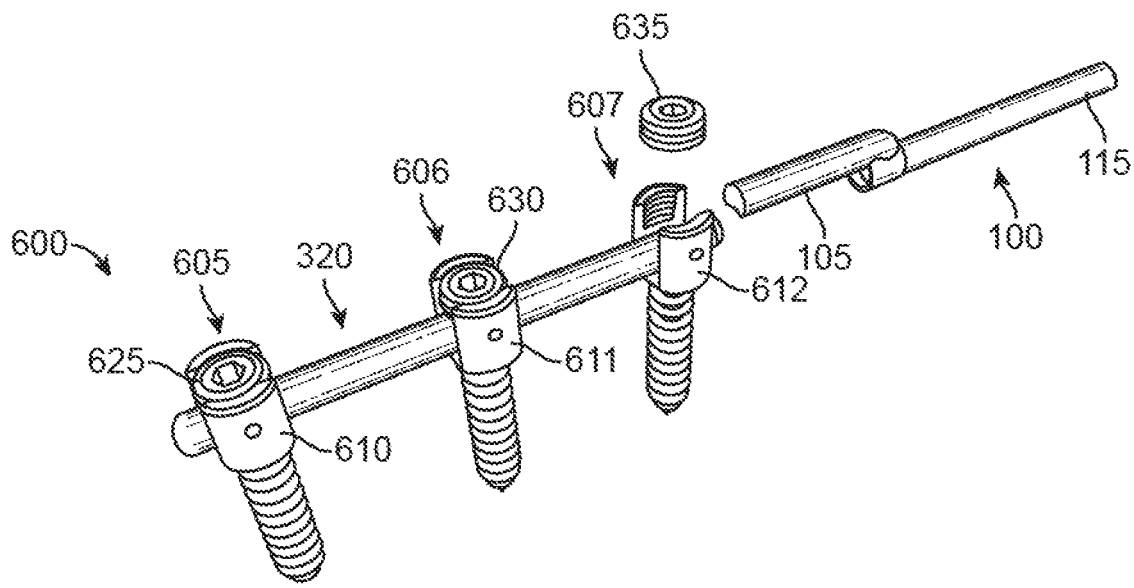
FIG. 20C depicts a spinal rod extension proximate to the third pedicle screw in accordance with an illustrative embodiment.

FIG. 20C is an angled top view of the existing two-level pedicle screw instrumentation construct 600 depicted in FIGS. 20A and 20B, with set screw 635 removed from screw head 612 in anticipation of a rod extension 100 being placed onto existing spinal rod 320 through pedicle screw head 612, in accordance with an illustrative embodiment. Locking cap 635 has been removed from pedicle screw head 612 of pedicle screw 607 in order to create space for the spinal rod extension 100 to mate to existing spinal rod 320. Pedicle screws 605 and 606 have locking caps 625 and 630 still engaged to pedicle screw heads 610 and 611, thus continuing to attach to rod 320. In an illustrative embodiment, a bottom portion of section 105 (i.e., connector portion) of the rod extension 100 can be curved or concave such that connector portion 105 form-fits the convex contour of the existing spinal rod 320 (see FIG. 6 and associated description). As such, when mounted to the existing spinal rod 320 (see FIG. 20D), the connector portion 105 can be flush or nearly flush with or within a top edge of the u-shaped pedicle screw head 612. The rod portion 115 of the rod extension 100 is then available to be secured to newly placed pedicle screws during a revision surgery (as shown in FIGS. 16-18).

Figure 20D:
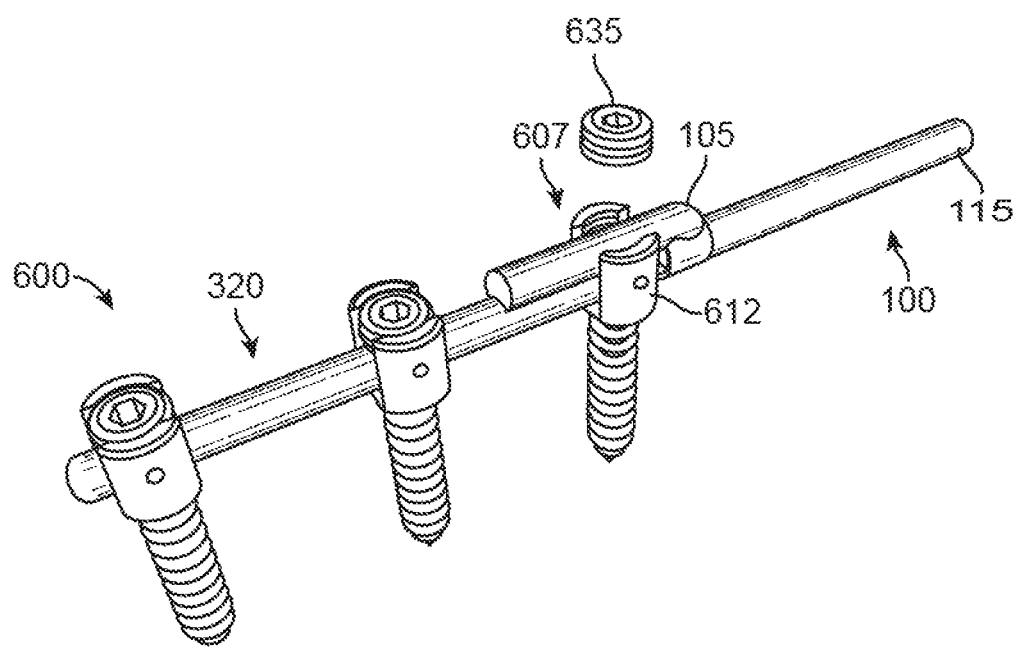
FIG. 20D depicts the spinal rod extension of FIG. 20C passed through the screw head of the third pedicle screw in accordance with an illustrative embodiment.

FIG. 20D is an angled top view of the existing two-level pedicle screw instrumentation construct 600 depicted in FIGS. 20A and 20B, with set screw 635 removed from the pedicle screw head 612, now with the connector portion 105 of rod extension 100 placed on the existing spinal rod 320 and passing through pedicle screw head 612, in accordance with an illustrative embodiment. The rod portion 115 of the rod extension 100 is then available to be secured to newly placed pedicle screws during a revision surgery (as shown in FIGS. 16-18).

FIGS. 21A-21E depict various views of a pedicle screw head connector 700 in accordance with illustrative embodiments. Pedicle screw head connector 700 attaches to an existing pedicle screw head and secures a rod extension to an existing rod (see FIGS. 24A-24B and FIGS. 25A-25C). FIG. 21A depicts an end wall 705 of the pedicle screw head connector 700, in accordance with an illustrative embodiment. An upper portion 706 of the end wall 705 includes a threaded portion 707 that accommodates a set screw (see FIG. 22A). A lower portion 708 of the end wall 705 includes a connector surface feature 709 that is designed to mate with a surface feature of a pedicle screw head, such as the surface feature 612A depicted in FIG. 20A, and later depicted in FIG. 22A. In an illustrative embodiment, the connector surface feature 709 is in the form of a semi-spherical protuberance that is sized to mate with a semi-spherical indentation on the pedicle screw head. Alternatively, the connector surface feature 709 may be an indentation that mates with a protuberance on the pedicle screw head. Additionally, regardless of whether the connector surface feature 709 is a protuberance or indentation, the connector surface feature may have a different shape such as square, rectangular, triangular, etc.

FIG. 21A also depicts a post 720 that extends from a body of the end wall 705 and that is used to secure the end wall 705 to a cross connector as described below. In an illustrative embodiment, each end wall includes a pair of posts (i.e., one on each side) such that the end wall can be mounted to a front cross connector and a rear cross connector. The post 720 can be integrally formed with the end wall 705. Alternatively, the post 720 may be mounted into a hole in the body of the end wall 705. While the post 720 is depicted as cylindrical, it is to be understood that other shapes (e.g., square, rectangular, star-shaped, etc.) may be used in other embodiments.

FIG. 21B depicts an angled top view of a pedicle screw head connector 700 that includes a pair of end walls 705 joined by a pair of cross connectors 715 that connect to end walls 705 by a pair of posts 720, the ends of which are visible, in accordance with an illustrative embodiment. The posts 720 are depicted in greater detail in FIGS. 22A-22E and FIGS. 23A-23D. As described herein, the posts 720 allow the end walls 705 to pivot (or articulate) relative to the cross connectors 715. FIG. 21C is an angled plane view of pedicle screw head connector 700 with the pair of end walls 705 and the cross connectors 715 that connect to the end walls 705 by posts 720, the ends of which are visible, in accordance with an illustrative embodiment. A single connector surface feature 709 that is designed to mate with a surface feature of a pedicle screw head, such as 612A as depicted in FIG. 20A, is visible on one of the end walls 705, but is not visible on the other end wall 705 due to the angle of the drawing. FIG. 21D is a bottom view of the pedicle screw head connector 700 with end walls 705 and cross connectors 715 that connect to the end walls 705 by posts 720, the ends of which are visible, in accordance with an illustrative embodiment. Connector surface features 709 that are designed to mate with surface features of a pedicle screw head, such as 612A depicted in FIG. 20A, are also visible. FIG. 21E is a top view of the pedicle screw head connector 700 with the end walls 705 and cross connectors 715 that connect to the end walls 705 by the posts 720, the ends of which are visible, in accordance with an illustrative embodiment.

FIG. 22A is an angled top view of the pedicle screw head connector 700 along with a set screw 636 and pedicle screw 607, in accordance with an illustrative embodiment. End walls 705 of the screw connector 700 are depicted in an angled configuration, articulating (or pivoting) through posts 720, the ends of which are shown here. In an illustrative embodiment, the posts 720 are integrally connected to the end walls 705. In an alternative embodiment, each post 720 is a cylindrical rod that extends through a hole in the first cross connector 715, through a cylindrical channel in the upper portion 706 of an end wall 705, and through a hole in the second cross connector 715. Alternatively, the pedicle screw head connector 700 may utilize 4 posts that extend through holes in the cross connectors 715 and into partial cylindrical channels in the upper portions 706 of the end walls 705. The posts 720 can be connected to the cross connectors 715 via a fiction fit, via pins (e.g. cotter pins placed through holes in the protruding ends of the posts 720) that prevent the cross connectors 715 from coming off of the posts 720, and/or by any other method.

The ability to pivot the end walls 705 allows the pedicle screw head connector 700 to slide onto pedicle screw head 612 of pedicle screw 607, as shown in FIG. 22B. When the angling of the end walls 705 is reversed (i.e., when lower portions of the end walls 705 are pivoted toward the pedicle screw head, as seen in FIGS. 22D-22E), a surface feature 709 (from FIGS. 21A and 21C) on the end walls 705 mates with a reciprocal surface feature on the pedicle screw head, creating a tight interference fit that is held by set screw 636. The set screw 636 is inserted into the threaded portion 707 (see FIGS. 21A and 21B) of the screw head connector 700, which forces the upper threaded portion of end walls 705 away from each other, reversing the articulation depicted in FIGS. 22A-22C. As shown, the surface features 709 of the end walls and the surface features 612a of the pedicle screw head are sized such that the screw head connector cannot be mounted to the screw head while end walls are orthogonal to the pair of cross connectors. The angling (or pivoting) of the end walls relative to the cross connectors allows the pedicle screw connector to slide a top surface of the pedicle screw head.

FIG. 22C depicts the pedicle screw head connector 700 slid onto the pedicle screw head 612 of pedicle screw 607, in anticipation of set screw 636 being inserted into threaded portions 707 of the end walls 705. FIG. 22D depicts the pedicle screw head connector 700 slid onto the pedicle screw head 612 of pedicle screw 607, now with set screw 636 being inserted into screw head connector 700 via screw threads 707 (see FIGS. 21A and 21B), in accordance with an illustrative embodiment. The process of set screw 636 engaging threaded portions 707 of the end walls 705 of the pedicle screw head connector 700 reverses the angulation of end walls 705, which in turn causes the inner surfaces of the end walls 705 (that include the surface features 709, see FIGS. 21A and 21C) to tightly engage and thus connect to the outer surfaces of the pedicle screw head 612 (that contain reciprocal surface features). Thus, insertion of set screw 636 creates an interference fit between the interfacing surfaces of the end walls 705 and the pedicle screw heads 612, and this fit is further enhanced by the reciprocal fit of the surface features 709 (from FIGS. 21A and 21C) of the end walls and the surface features of the pedicle screw head. The cumulative effect of these interfaces is to establish a connection of screw head connector 700 to pedicle screw head 612. FIG. 22E depicts set screw 636 fully inserted into screw head connector 700, which fully establishes the connection between screw head connector 700 and pedicle screw head 612, in accordance with an illustrative embodiment. Not shown is the presence of rod 320 and mated rod extension 100 in slot 769 of pedicle screw head 612; these features are shown in FIG. 24B.

Figure 23A:
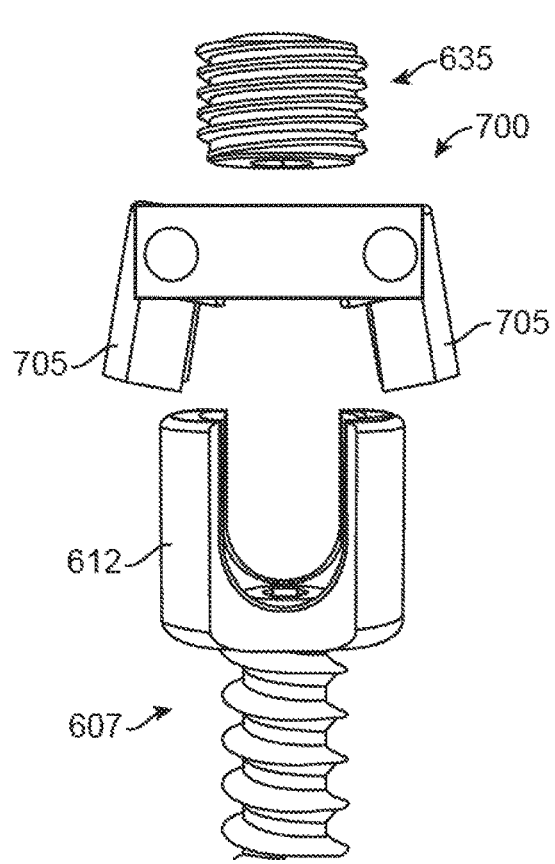
FIG. 23A depicts a pedicle screw head connector with end walls in an angled position in accordance with an illustrative embodiment.
Figure 23B:
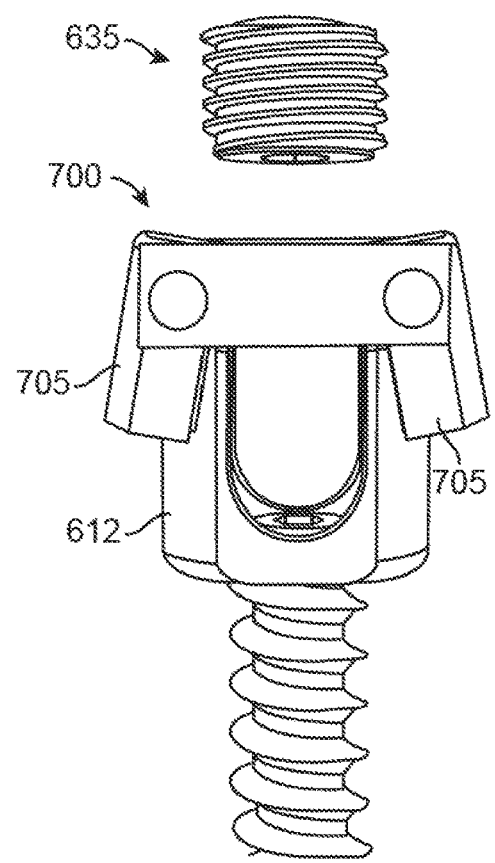
FIG. 23B depicts placement of the pedicle screw head connector of FIG. 23A onto a pedicle screw in accordance with an illustrative embodiment.
Figure 23C:
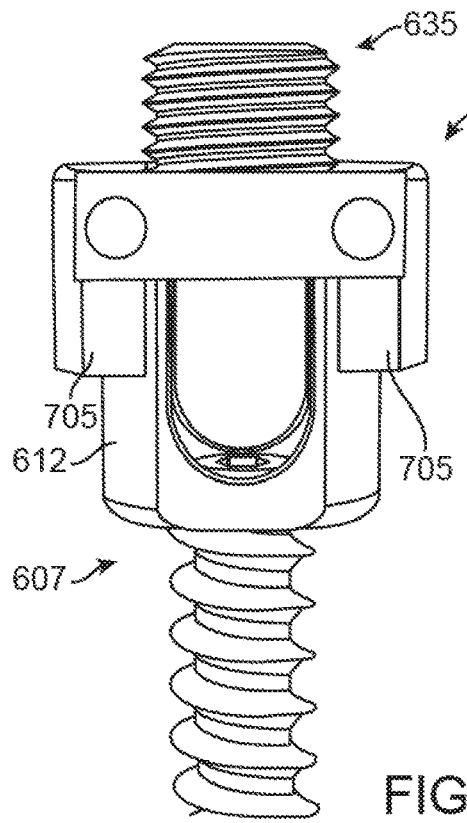
FIG. 23C depicts the pedicle screw head connector on the pedicle screw with a partially threaded set screw in accordance with an illustrative embodiment.
Figure 23D:
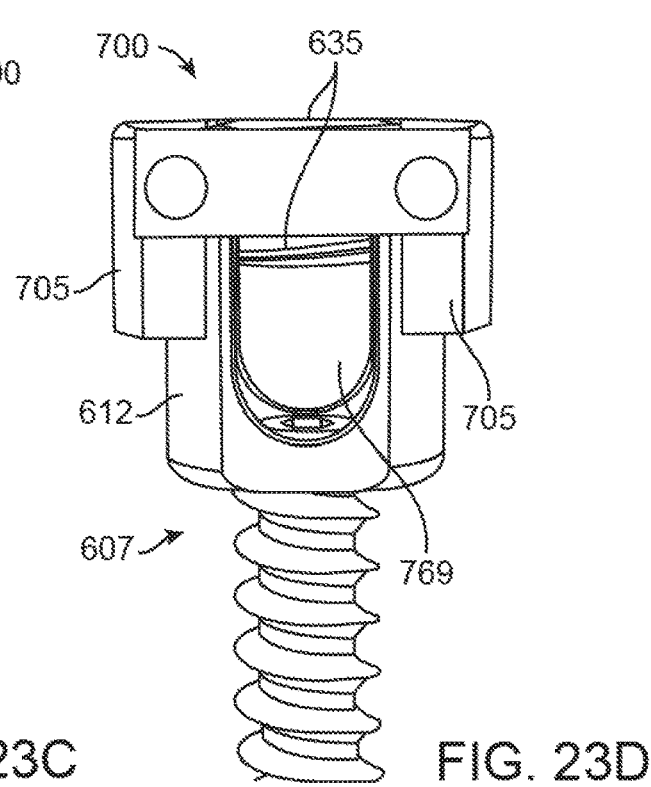
FIG. 23D depicts the pedicle screw head connector on the pedicle screw with a fully threaded set screw in accordance with an illustrative embodiment.

FIG. 23A depicts a cephalad-caudal or end view of pedicle screw head connector 700 with end walls 705, the set screw 636 not yet advanced into screw head connector 700, and the pedicle screw 607 with pedicle screw head 612, in accordance with an illustrative embodiment. The end walls 705 are in an angled position, allowing placement of screw head connector 700 onto screw head 612 in anticipation of placement of set screw 636, as depicted in FIG. 23B, in accordance with an illustrative embodiment. In one embodiment, the angled configuration can refer to an angle of greater than 90 degrees (e.g., an angle between 90 degrees and 180 degrees) between each of the end walls and the cross connectors (as shown in the view of FIG. 23A). Reversing the angled configuration can result in an angle of approximately 90 degrees (e.g., an angle between 85-95 degrees) between each of the end walls and the cross connectors (as shown in FIG. 23C). In alternative embodiments, different angles may be used.

FIG. 23C depicts a cephalad-caudal view of pedicle screw head connector 700 with angulation of the end walls 705 reversed as set screw 636 is inserted, and a pedicle screw 607 with pedicle screw head 612, in accordance with an illustrative embodiment. Pedicle screw head connector 700 is attaching to pedicle screw head 612 of pedicle screw 607, due to set screw 636 being inserted into screw head connector 700 via screw threads 707 (see FIGS. 21A and 21B). The process of set screw 636 engaging threaded portions 707 of the end walls 705 of screw head connector 707 (see FIGS. 21A and 21B, and FIG. 22D) reverses the angulation of the end walls 705, which in turn causes the inner surfaces of the end walls 705 (that include surface features 709, see FIGS. 21A and 21C) to tightly engage and thus connect to the outer surfaces of screw head 612 (that contain reciprocal surface features, see FIGS. 20A and 22A). The insertion of set screw 636 reverses the angulation of the end walls 705, creating an interference fit between the interfacing surfaces of end walls 705 and pedicle screw head 612, and this fit is further enhanced by the reciprocal fit of the surface features as described herein. The cumulative effect of these interfaces establishes a connection of screw head connector 700 with pedicle screw head 612. FIG. 22E depicts set screw 636 fully inserted into screw head connector 700, which fully establishes the connection between screw head connector 700 and pedicle screw head 612. Not shown is the presence of rod 320 and mated rod extension 100 in slot 769 (shown earlier in FIGS. 20C and 20D, and later in FIG. 24B).

FIG. 24A is an angled side view of screw head connector 700, pedicle screw 607 with pedicle screw head 612, existing rod 320, and rod extension 100, in accordance with an illustrative embodiment. Rod extension 100 is passed through pedicle screw head 612, in anticipation of screw head connector 700 being attached to screw head 612.

FIG. 24B is an angled side view of screw head connector 700, pedicle screw 607 with pedicle screw head 612, existing rod 320, and rod extension 100, in accordance with an illustrative embodiment. Rod extension 100 is passed through pedicle screw head 612, now with screw head connector 700 secured to screw head 612 by virtue of set screw 636 placement (see FIGS. 23A-23D), which in turn presses rod extension 100 firmly against existing rod 320 and secures rod extension 100 and existing rod 320 within pedicle screw head 612.

When set screw 636 is inserted into the threaded portion of screw head connector 700 (see FIGS. 21A-21B), a surface of set screw 636 presses against an upper surface of rod extension 100, which in turn presses a surface of rod extension 100 to a surface of existing rod 320 and this in turn presses a surface of existing rod 320 to a surface of pedicle screw head 612, creating a tight frictional fit amongst screw head connector 700, set screw 636, screw head 612, existing rod 320, and rod extension 100. When set screw 636 is fully inserted, this creates a frictional fit between surface feature 709 (see FIG. 21A and FIG. 21C) of the screw head connector and the corresponding surface feature 612a (see FIG. 20A and FIG. 22A) of the pedicle screw head 612. This further secures screw head connector 700, pedicle screw head 612 and associated pedicle screw 607, existing rod 320, and rod extension 100 to each other via frictional forces (see FIGS. 22C and 22D and associated descriptions). The rod portion 115 of rod extension 100 is then available to be secured to newly placed pedicle screws during a revision surgery (as shown in FIGS. 16-18).

Figure 25A:
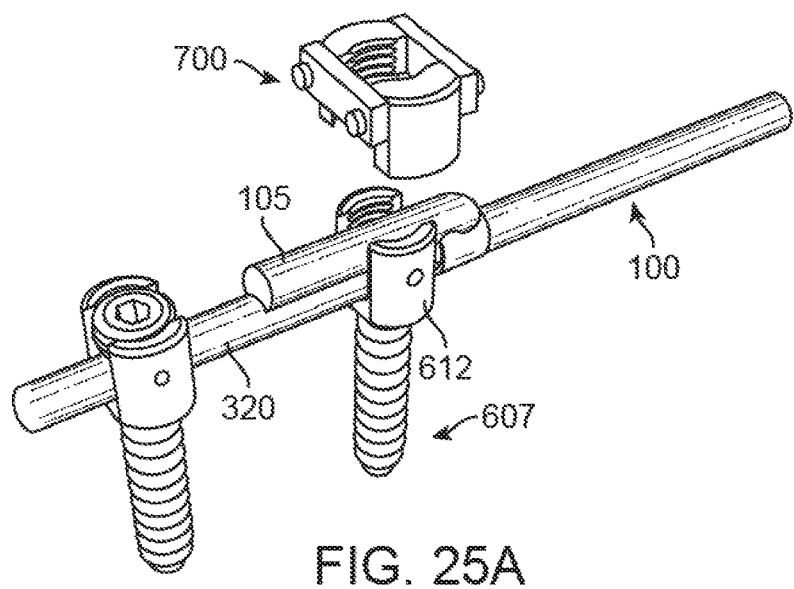
FIG. 25A is an angled top view of a pedicle screw head connector adjacent to a rod extension positioned in a pedicle screw head in accordance with an illustrative embodiment.

FIG. 25A is an angled top view of screw head connector 700, pedicle screw 607 with pedicle screw head 612, existing rod 320 (see FIG. 20D), and rod extension 100 (see FIG. 20D), in accordance with an illustrative embodiment. The connector portion 105 of rod extension 100 is passed through pedicle screw head 612 (see FIGS. 1, 2, 7, 8, and 11) in anticipation of screw head connector 700 being attached to screw head 612.

Figure 25B:
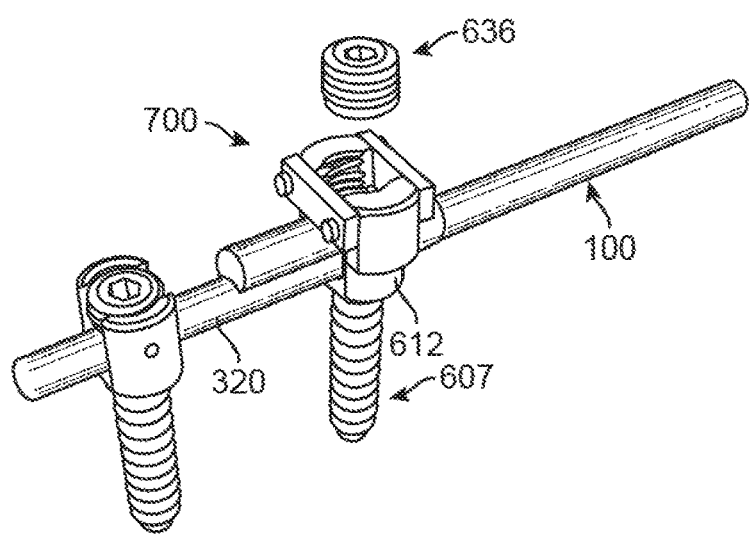
FIG. 25B is an angled top view of the pedicle screw head connector placed onto the pedicle screw head in accordance with an illustrative embodiment.

FIG. 25B is an angled top view of screw head connector 700, set screw 636, pedicle screw 607 with pedicle screw head 612, existing rod 320, and rod extension 100, in accordance with an illustrative embodiment. In FIG. 25B, the screw head connector 700 has been placed onto screw head 612, in anticipation of being secured to screw head 612 by set screw 636.

Figure 25C:
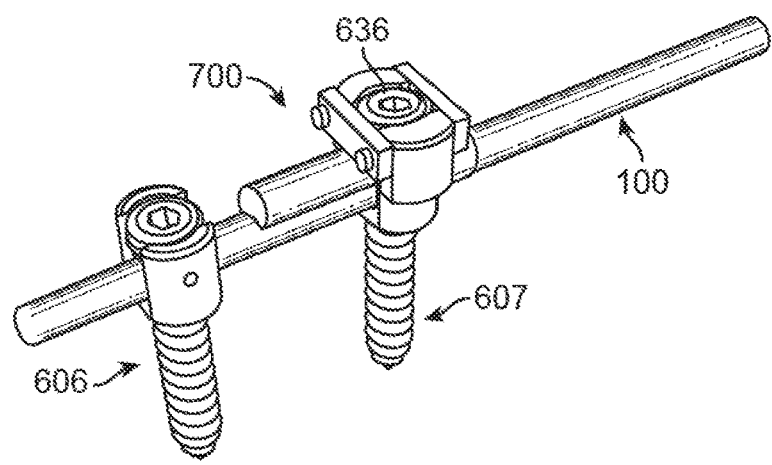
FIG. 25C is an angled top view of the pedicle screw head connector mounted onto the pedicle screw head with a set screw in accordance with an illustrative embodiment.

FIG. 25C depicts an angled top view of screw head connector 700, set screw 636, pedicle screw 607 with pedicle screw head 612, existing rod 320, and rod extension 100, in accordance with an illustrative embodiment. Screw head connector 700 is secured to screw head 612 by virtue of set screw 636 placement (see FIGS. 22A-22D and FIGS. 23A-23D), which in turn presses a surface of rod extension 100 firmly against a surface of existing rod 320 which is in turn pressed against a surface of screw head 612, securing rod extension 100 and existing rod 320 within pedicle screw head 612.

Figure 26A:
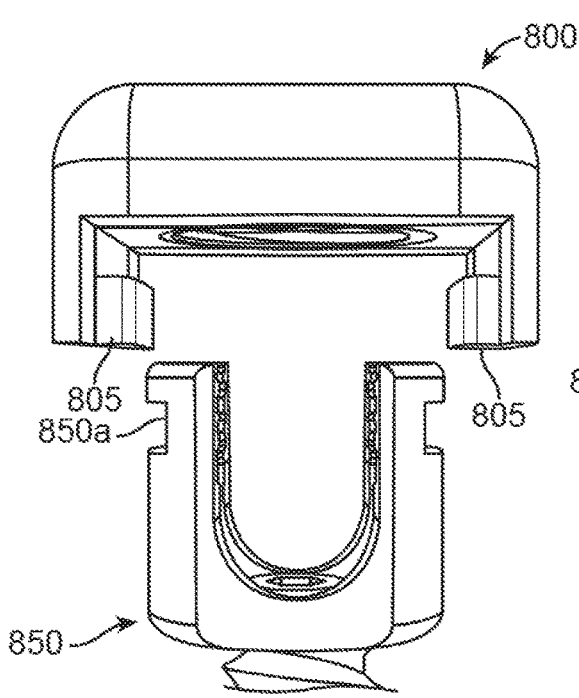
FIG. 26A is an end view depicting an alternative configuration of a pedicle screw head connector and pedicle screw in accordance with an illustrative embodiment.

FIG. 26A depicts a cephalad-caudal or end view of an alternative embodiment of a screw head connector 800 and a pedicle screw head 850 in a disassembled configuration, in accordance with illustrative embodiments. Pedicle screw head 850 includes a surface feature 850a of variable shape, here a notch, designed to allow instruments to be reversibly and temporarily attached to the pedicle screw head. The surface feature 850a is positioned on the end walls that extend from a cap of the screw head connector 800. In alternative implementations, the surface feature on the pedicle screw head 850 may be a protuberance as opposed to an indentation, and the protuberance/indentation can have another shape and/or dimension. The surface feature 850a creates a connection point for instruments which are typically used for pedicle screw insertion and/or reduction of the rod into the pedicle screw head during a surgery, after which the instrument(s) is/are detached from the pedicle screw head. Screw head connector 800 includes protuberances 805 that are designed to mate with the surface features 850a of the pedicle screw head 850.

Figure 26B:
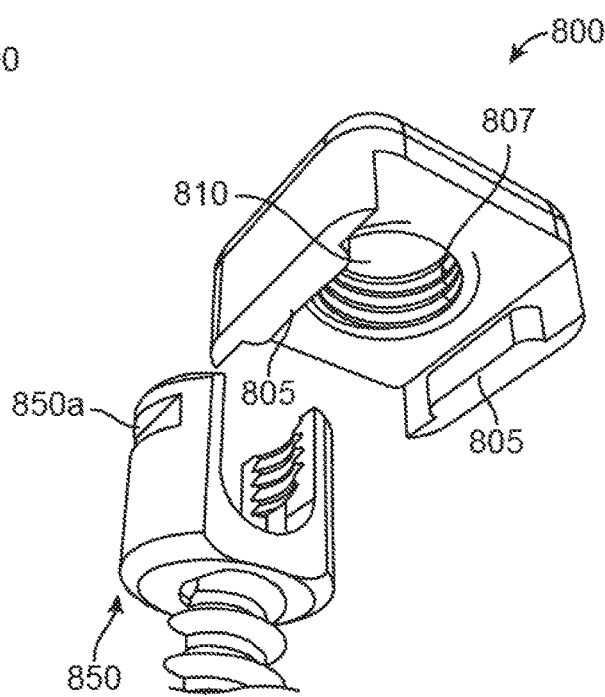
FIG. 26B is an angled bottom view of the pedicle screw head connector and the pedicle screw of FIG. 26A in accordance with an illustrative embodiment.

FIG. 26B depicts an angled bottom view of screw head connector 800 and a pedicle screw head 850 in a disassembled configuration, in accordance with an illustrative embodiment. As discussed above, the pedicle screw head 850 includes the surface feature 850a, designed to allow instruments to be reversibly and temporarily attached to the pedicle screw head. The surface feature 850a creates a connection point for instruments which are typically used for pedicle screw insertion and/or reduction of the rod into the pedicle screw head during a surgery, after which the instrument(s) is/are detached from the pedicle screw head. Screw head connector 800 includes surface features 805 that are designed to mate with the surface features 850a of the pedicle screw head. The cap of the screw head connector 800 also includes a hole 810 with threads 807 designed to accommodate a set screw.

Figure 26C:
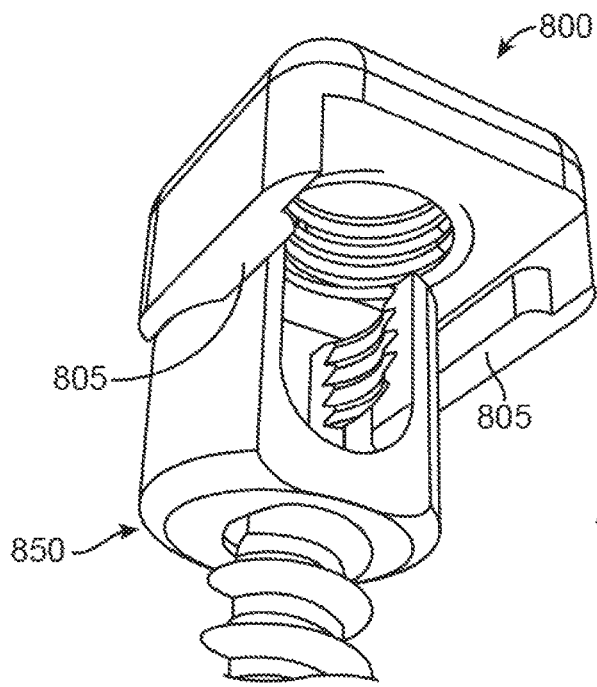
FIG. 26C is an angled bottom view of the pedicle screw head connector partially placed onto the pedicle screw in accordance with an illustrative embodiment.

FIG. 26C is an angled bottom view of screw head connector 800 and a pedicle screw head 850 in an assembling configuration, in accordance with an illustrative embodiment. The surface features 805 of the screw head connector 800 are now shown in the process of mating with the surface features 850a of the pedicle screw head 850. As shown, in this embodiment, the end walls of the pedicle screw head connector 800 are rigid and do not pivot relative to the cap of the pedicle screw head connector 800. The assembly is therefore performed by sliding the pedicle screw head connector 800 onto the pedicle screw head 850 such that the surface features 850a mate with the surface features 805.

Figure 26D:
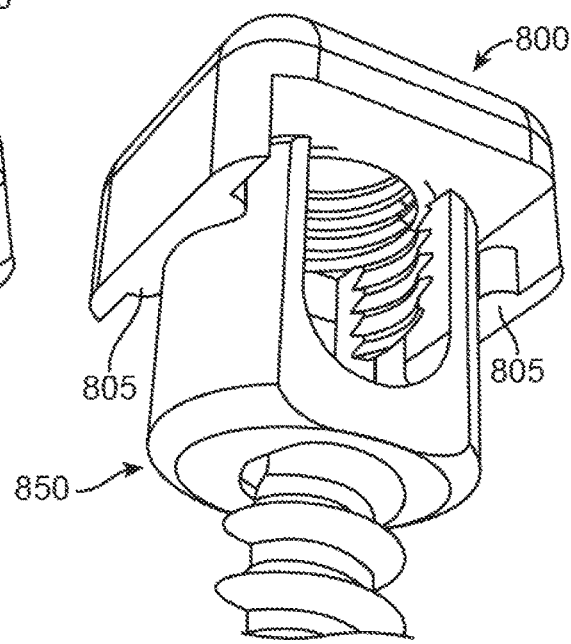
FIG. 26D is an angled bottom view of the pedicle screw head connector fully placed onto the pedicle screw in accordance with an illustrative embodiment.

FIG. 26D is an angled bottom view of screw head connector 800 and a pedicle screw head 850 in an assembled configuration, in accordance with an illustrative embodiment. Surface features 805 of the pedicle screw head connector 850 are now shown mating with the surface features 850a in pedicle screw head 850 as seen in FIGS. 26A and 26B.

Figures 27A, 27B:
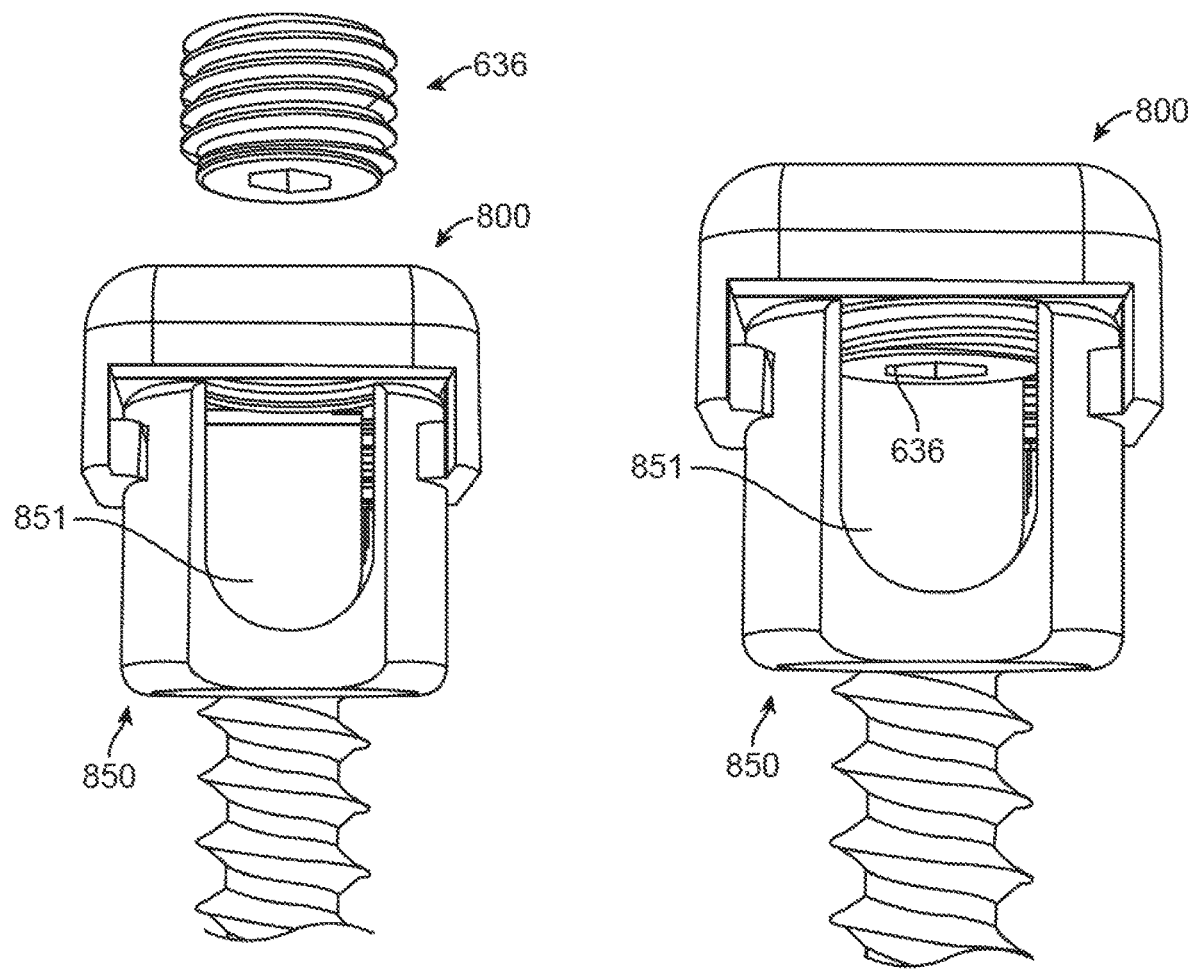
FIG. 27A depicts an end view of the pedicle screw head connector of FIG. 26A assembled onto the pedicle screw head in anticipation of set screw placement in accordance with an illustrative embodiment.
FIG. 27B depicts the pedicle screw head connector attached to the pedicle screw head with a set screw in accordance with an illustrative embodiment.

FIG. 27A depicts an end view of screw head connector 800 and a pedicle screw head 850 in an assembled configuration in anticipation of set screw 636 placement, in accordance with an illustrative embodiment. An existing rod (not shown, see FIG. 27C) and a rod extension (not shown, see FIG. 27C) will pass through a slot 851 in pedicle screw head 850 (see FIG. 27C and FIGS. 28A-28C).

FIG. 27B depicts an end view of screw head connector 800 and a pedicle screw head 850 in an assembled configuration, with set screw 636 now placed into the screw head connector threads (See FIG. 26B) of screw head connector 800 and threads of the pedicle screw head 850, in accordance with an illustrative embodiment. An existing rod (not shown, see FIG. 27C) and a rod extension (not shown, see FIG. 27C) will pass through slot 851 in pedicle screw head 850 (see FIG. 27C and FIGS. 28A-28C).

Figure 27C:
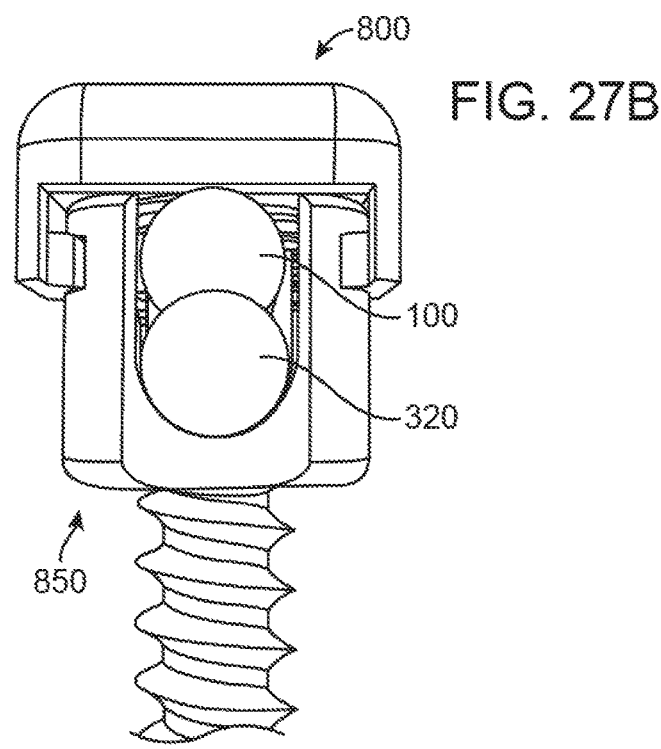
FIG. 27C depicts the pedicle screw head connector attached to the pedicle screw to secure a rod extension to an existing spinal rod in accordance with an illustrative embodiment.

FIG. 27C depicts an end view of screw head connector 800 and a pedicle screw head 850 in an assembled configuration, now with rod extension 100 and existing rod 320 depicted in opening 851 (from FIGS. 27A and 27B) in pedicle screw head 850, in accordance with an illustrative embodiment. A surface of set screw 636 presses against a surface of rod extension 100 (see also FIG. 28C), which in turn presses against a surface of existing rod 320, which in turn presses against a surface of pedicle screw head 850, thus creating a tight frictional fit amongst screw head connector 800, screw head 850, rod extension 100, and existing rod 320 (see FIGS. 28A-28C).

Figure 28A:
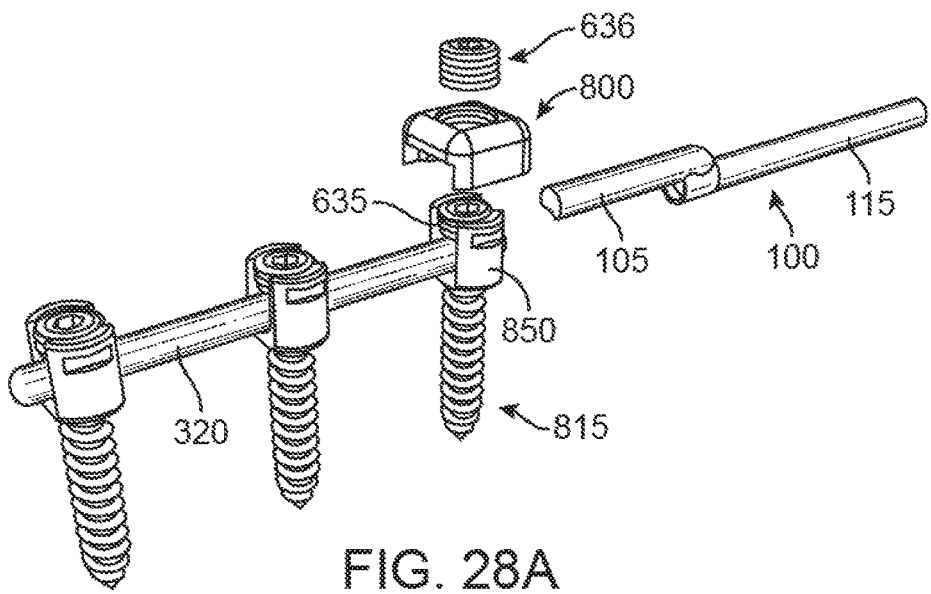
FIG. 28A depicts the pedicle screw head connector and set screw proximate to an existing spinal rod and a rod extension in accordance with an illustrative embodiment.

FIG. 28A depicts an angled top view of screw head connector 800, pedicle screw 815 with pedicle screw head 850, existing rod 320 (see FIG. 20D), and rod extension 100 (see FIG. 20D in accordance with an illustrative embodiment. Existing rod 320 is still attached to pedicle screw head 850 via set screw 635. Screw head connector 800 and associated set screw 636 and rod extension 100 are in a disassembled position, in anticipation of set screw 635 being removed, allowing placement of rod extension 100 through pedicle screw head 850 and onto existing rod 320 (analogous to the configuration seen in FIG. 20D).

Figure 28B:
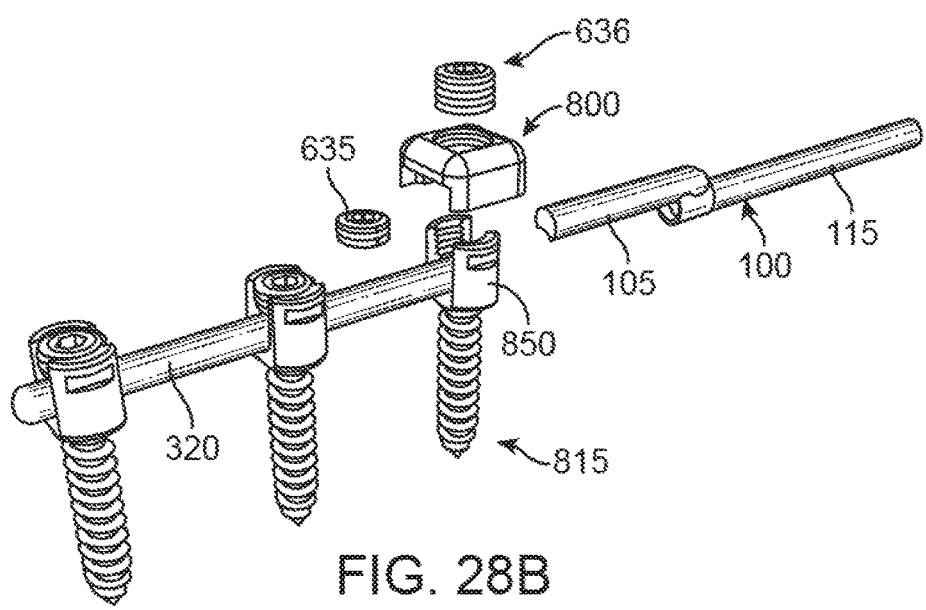
FIG. 28B depicts the configuration of FIG. 28A with an existing set screw removed from the pedicle screw head in accordance with an illustrative embodiment.

FIG. 28B depicts an angled top view of screw head connector 800, pedicle screw 815 with pedicle screw head 850, existing rod 320, and rod extension 100, in accordance with an illustrative embodiment. Set screw 635 has been removed from pedicle screw head 850, which will allow for the connector portion 105 of rod extension 100 to be placed through pedicle screw head 850 and rest on existing rod 320 (analogous to the configuration seen in FIG. 20D). Screw head connector 800 and associated set screw 636 and rod extension 100 are in a disassembled position, in anticipation of placement of the connector portion 105 of rod extension 100 through pedicle screw head 850 and onto existing rod 320 (analogous to the configuration seen in FIG. 20D).

Figure 28C:
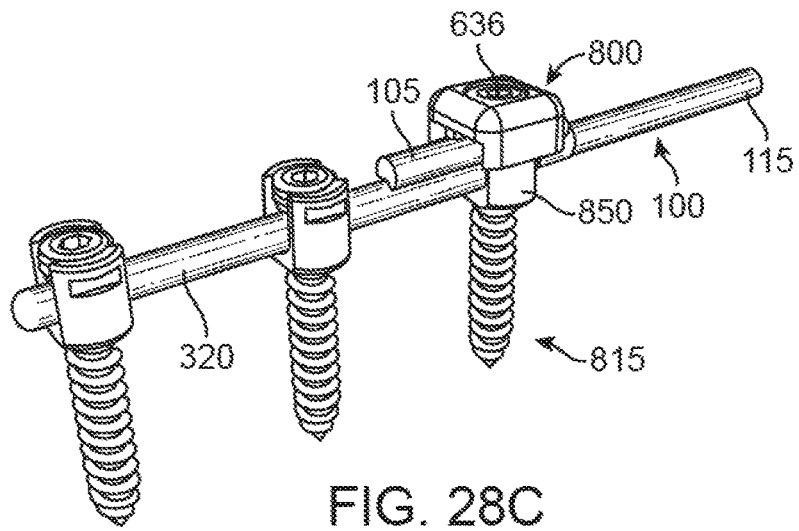
FIG. 28C depicts the configuration of FIG. 28B with the pedicle screw head connector mounted onto the pedicle screw head to secure the rod extension to the existing spinal rod in accordance with an illustrative embodiment.

FIG. 28C depicts an angled top view of screw head connector 800, pedicle screw 815 with pedicle screw head 850, existing rod 320, and rod extension 100, in accordance with an illustrative embodiment. The connector portion 105 of rod extension 100 has been placed through pedicle screw head 850 and rests on existing rod 320 (analogous to the configuration seen in FIG. 20D). Screw head connector 800 is secured to pedicle screw head 850 by set screw 636, which when inserted presses against an upper surface of rod extension section 105, which in turn presses a surface of rod extension 105 to a surface of existing rod 320 and presses a surface of existing rod 320 to a surface of pedicle screw head 850, creating a tight frictional fit amongst screw head connector 850, set screw 636, screw head 850, existing rod 320, and rod extension 100. When set screw 636 is tightly secured against a surface of rod extension 100, this creates a further frictional fit between a surface of surface feature 805 (see FIG. 26A-26D) and an opposing surface feature 850a (see FIGS. 26A-26D), which are forced in opposite directions, further securing screw head connector 800, screw head 850 and associated pedicle screw 815, existing rod 320, and rod extension 100 to each other via frictional forces. The rod portion 115 of rod extension 100 is then available to be secured to newly placed pedicle screws during a revision surgery (see FIGS. 16-18).

Figure 29:
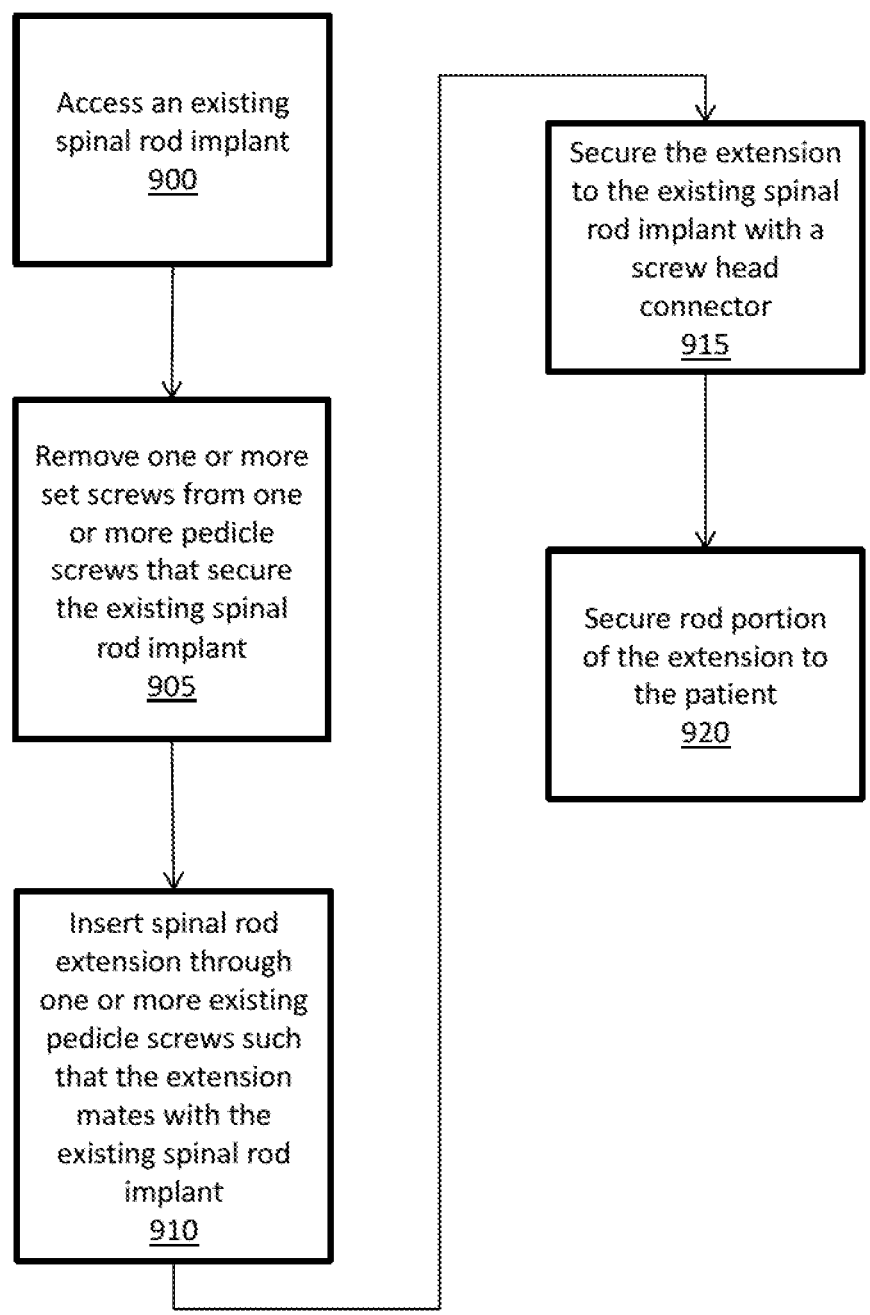
FIG. 29 is a flow diagram depicting a process for mounting a spinal rod extension to an existing spinal rod in accordance with another illustrative embodiment.

FIG. 29 is a flow diagram depicting a process for mounting a spinal rod extension to an existing spinal rod in accordance with an illustrative embodiment. In alternative embodiments, fewer, additional, and/or different operations may be performed. Additionally, the use of a flow diagram is not meant to be limiting with respect to the order of operations performed.

In an operation 900, the surgeon accesses an existing spinal rod implant in a patient. Specifically, the surgeon can surgically approach the top or the bottom of the existing spinal rod and terminal pedicle screw, depending on where the spinal rod extension is to be placed. In an operation 905, the surgeon removes one or more set screws (or locking caps) from one or more pedicle screws that secure the existing spinal rod. Upon removal of the one or more set screws, all or a portion of the existing spinal rod is exposed.

In an operation 910, the surgeon inserts a connector portion of a spinal rod extension through the one or more existing pedicle screws from which the one or more set screws were removed. Specifically, the connector portion of the spinal rod extension is placed dorsally onto the existing spinal rod, passing through the pedicle screw u-shaped head(s) from which the set screw(s) have been removed.

In an operation 915, the connector portion of the spinal rod extension is secured to the existing spinal rod implant. In an illustrative embodiment, the spinal rod extension is secured to the existing spinal rod with one or more screw head connectors, as described herein. In alternative embodiments, a different securing method may be used.

In an operation 920, the surgeon secures the rod portion of the spinal rod extension to the patient. In an illustrative embodiment, the rod portion of the spinal rod extension is attached to new pedicle screws that are placed cephalad or caudal to the existing spinal rod, depending on the needs of the patient. The rod portion of the spinal rod extension can be tunneled beneath the skin, subcutaneous tissues, and muscle of the patient in order to attach to the new pedicle screws that have been placed percutaneously. Alternatively, the rod portion of the spinal rod implant can be attached to new pedicle screws that have been placed through a conventional open posterior approach.

The spinal rod extensions described herein can be made of the same materials as existing spinal instrumentation systems, which include but are not limited to titanium, titanium alloy, cobalt chrome, stainless steel, and polyether ether ketone (PEEK). The spinal rod extension can be provided as a straight version (i.e., a version in which the rod portion of the spinal rod extension is substantially straight) that can be placed as-is into the patient. The spinal rod extension can also be flexible such that the rod portion of the spinal rod extension can be bent prior to implantation in order to match the patient's anatomy. The spinal rod extension can also be provided as a precontoured version in which the rod portion is pre-bent to match a patient's lordotic or kyphotic spine segment. The spinal rod extension can also include an articulation such that the portion of the spinal rod extension that is attached to new pedicle screws can be angled with respect to the portion of the rod extension that is attached to the previously placed rod.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A spinal rod extension system comprising:
a rod portion of a spinal rod extension;
a connector portion connected to the rod portion, wherein the connector portion is configured for insertion through a screw head of an existing pedicle screw that is used to secure an existing spinal rod; and
a screw head connector configured to mount to the screw head of the existing pedicle screw to secure the connector portion to the existing spinal rod, wherein the screw head connector includes a cap, and a first end wall and a second end wall that are connected to the cap, wherein the first end wall includes a first surface feature and the screw head includes a second surface feature, and wherein the first surface feature mates with the second surface feature to secure the screw head connector to the screw head.

2. The system of claim 1, wherein the first end wall and the second end wall are rigidly connected to the cap.

3. The system of claim 1, wherein the cap of the screw head connector includes a threaded hole.

4. The system of claim 3, wherein threads of the threaded hole match a threaded portion of the screw head.

5. The system of claim 4, further comprising a set screw that threads into the threaded hole of the cap and the threaded portion of the screw head to secure the screw head connector to the screw head.

6. The system of claim 5, wherein the set screw contacts a surface of the connector portion and secures the connector portion to the existing spinal rod.

7. The system of claim 1, wherein the first surface feature comprises a protuberance and the second surface feature comprises an indentation configured to receive the protuberance.

8. The system of claim 1, wherein the second surface feature comprises a protuberance and the first surface feature comprises an indentation configured to receive the protuberance.

9. The system of claim 1, wherein the connector portion includes a concave surface configured to mate with the existing spinal rod.

10. A screw head connector comprising:
a cap that includes a threaded hole, wherein threads of the threaded hole match a threaded portion of a pedicle screw head;
a first end wall and a second end wall rigidly connected to the cap;
a first surface feature mounted on an interior surface of the first end wall and a second surface feature mounted on an interior surface of the second end wall, wherein the first surface feature and the second surface feature are configured to mate with corresponding surface features on the pedicle screw head; and a set screw that threads into the threaded hole in the cap and into the threaded portion of the pedicle screw head to secure the screw head connector to the pedicle screw head.

11. The screw head connector of claim 10, wherein the corresponding surface features on the pedicle screw head are positioned on an outer wall of the pedicle screw head.

12. The screw head connector of claim 10, wherein the first surface feature comprises a protuberance or an indentation.

* * * * *